US008475814B2

(12) United States Patent
Rouanet et al.

(10) Patent No.: US 8,475,814 B2
(45) Date of Patent: *Jul. 2, 2013

(54) PREVENTION AND TREATMENT OF BREAST CANCER WITH 4-HYDROXY TAMOXIFEN

(75) Inventors: Philippe Rouanet, Monpellier (FR); Dominique Salin Drouin, Verriere le Biosson (FR); Jacques Wepierre, Grisy Suisnes (FR)

(73) Assignee: Besins Healthcare Luxembourg SARL, Luxembourg (LU)

( * ) Notice: Subject to any disclaimer, the term of this patent is extended or adjusted under 35 U.S.C. 154(b) by 314 days.

This patent is subject to a terminal disclaimer.

(21) Appl. No.: 12/353,890

(22) Filed: Jan. 14, 2009

(65) Prior Publication Data
US 2009/0186944 A1    Jul. 23, 2009

Related U.S. Application Data

(62) Division of application No. 10/734,638, filed on Dec. 15, 2003, now Pat. No. 7,704,516.

(60) Provisional application No. 60/458,963, filed on Apr. 1, 2003.

(51) Int. Cl.
*A61K 8/02* (2006.01)
*A61K 31/05* (2006.01)

(52) U.S. Cl.
USPC .......................................... 424/401; 514/736

(58) Field of Classification Search
USPC .......................................... 424/401; 514/736
See application file for complete search history.

(56) References Cited

U.S. PATENT DOCUMENTS

| | | | |
|---|---|---|---|
| 4,919,937 A | 4/1990 | Mauvais-Jarvis et al. |
| 4,973,755 A | 11/1990 | Grafe et al. |
| 5,045,553 A | 9/1991 | Ueda et al. |
| 5,189,212 A | 2/1993 | Ruenitz |
| 5,613,958 A | 3/1997 | Kochinke et al. |
| 5,720,963 A | 2/1998 | Smith |
| 5,904,930 A | 5/1999 | Fischer et al. |
| 5,945,109 A | 8/1999 | Schmidt et al. |
| 6,013,270 A | 1/2000 | Hargraves et al. |
| 6,503,894 B1 | 1/2003 | Dudley et al. |
| 7,485,623 B2 | 2/2009 | Bua |
| 7,507,769 B2 | 3/2009 | Nestour |
| 7,704,516 B2 | 4/2010 | Drouin et al. |
| 7,767,717 B2 | 8/2010 | Palumbo et al. |
| 7,786,172 B2 | 8/2010 | De Lignieres |
| 7,968,532 B2 | 6/2011 | Le Nestour et al. |
| 2003/0087885 A1 | 5/2003 | Masini-Eteve et al. |
| 2003/0175329 A1 | 9/2003 | Azarnoff et al. |
| 2004/0086552 A1 | 5/2004 | Klokkers et al. |
| 2004/0198706 A1 | 10/2004 | Carrara et al. |
| 2005/0031695 A1 | 2/2005 | Rouanet et al. |
| 2005/0032909 A1 | 2/2005 | Lignieres et al. |
| 2005/0032910 A1 | 2/2005 | Palumbo et al. |
| 2005/0158388 A1 | 7/2005 | Le Nestour et al. |
| 2005/0208133 A1 | 9/2005 | Hilt et al. |
| 2006/0105041 A1 | 5/2006 | Masini-Eteve et al. |
| 2009/0203796 A1 | 8/2009 | Le Nestour et al. |

FOREIGN PATENT DOCUMENTS

| | | |
|---|---|---|
| DE | 38 36 862 A1 | 5/1990 |
| EP | 0 513 832 B1 | 7/2000 |
| WO | WO 95/24187 | 9/1995 |
| WO | WO 97/36570 | 10/1997 |
| WO | WO 99/33451 A2 | 7/1999 |
| WO | WO 01/43775 A2 | 6/2001 |

OTHER PUBLICATIONS

Alberti et al., "In Vivo Assessment of Enhanced Topical Delivery of Terbinafine to Human Stratum Corneum," *J. of Controlled Release*, 71:319-327 (2001).
J. Barrat et al., "Effet in vivo de l'administration locale de progestérone sur l'activité mitotique des galactophores humains", J. Gynecol. Obstet. Biol. Reprod. 19: 269-274 1990.
Bronaugh & Maibach, "Percutaneous Absorption Drugs-Cosmetics-Mechanisms-Methodology", Marcel Dekker Inc., New York, 1999.
Philip Carthew et al., "Cumulative exposure to tamoxifen: DNA adducts and liver cancer in the rat", Arch Toxicol (2001) 75: 375-380.
Gerard Chetrite et al., "Effect of Promegestone, Tamoxifen, 4-Hydroxytamoxifen and ICI 164,384 on the Oestrone Sulphatase Activity of Human Breast Cancer Cells", Anticancer Research 13: 931-934 (1993).
Eric C. Dietze et al., "Tamoxifen but Not 4-Hydroxytamoxifen Initiates Apoptosis in p53(−) Normal Human Mammary Epithelial Cells by Inducing Mitochondrial Depolarization", The Journal of Biological Chemistry vol. 276, No. 7, Issue of Feb. 16, 2001, pp. 5384-5394.
I.S. Fentiman et al., "Dosage and duration of tamoxifen treatment for mastalgia: a controlled trial", Br. J. Surg. Sep. 1988, vol. 75, No. 9, pp. 845-846.
I.S. Fentiman et al., "Studies of tamoxifen in women with mastalgia", The British Journal of Clinical Practice, Supplement 68, vol. 43, No. 11, Nov. 1989, pp. 34-36.
N. Giambiagi et al., "Immunological Differences Between the Estradiol-, Tamxifen—and 4-Hydroxy-Tamoxifen-Estrogen Receptor Complexes Detected by Two Monoclonal Antibodies", J. Steroid Biochem. vol. 30, No. 1-6, pp. 213-217, 1988.
V. Craig Jordan et al., "Metabolites of tamoxifen in animals and man: identification, pharmacology, and significance", Breast Cancer Research and Treatment, 2, pp. 123-138.
George G.J.M. Kuiper et al., "Comparison of the Ligand Binding Specificity and Transcript Tissue Distribution of Estrogen Receptors α and β", Endocrinology, vol. 138, No. 3, 1997, pp. 863-870.
Frédérique Kuttenn et al., "Médecine Et Thérapeutique", C.R. Acad. Sc. Paris, , Série III, No. 12, 1985, 300:457-461.

(Continued)

*Primary Examiner* — Renee Claytor
(74) *Attorney, Agent, or Firm* — Foley & Lardner LLP

(57) ABSTRACT

Pharmaceutical compositions of 4-hydroxy tamoxifen, particularly compositions suitable for percutaneous administration, are useful in methods for treating and preventing breast cancer. When percutaneously administered to a patient's breasts, 4-hydroxy tamoxifen concentrates locally, and exerts an anti-estrogenic effect. In patients with breast cancer, this effect reduces tumor tissue proliferation. In patients at risk for developing breast cancer, the anti-estrogenic effect prevents breast tumor formation.

20 Claims, 3 Drawing Sheets

OTHER PUBLICATIONS

Kuttenn et al., Basis for percutaneous administration of antiestrogens in breast pathology, >> *Contraception Fertilite Sexualite*, vol. 19, No. 2, 1991.

Catherine Malet et al., "Tamoxifen and Hydroxytamoxifen Isomers versus Estradiol Effects on Normal Human Breast Cells in Culture", Cancer Research, vol. 48, No. 24, Dec. 15, 1988, pp. 7193-7199.

Pierre Mauvais-Jarvis et al., "trans-4-Hydroxytamoxifen Concentration and Metabolism after Local Percutaneous Adminstration to Human Breast", Cancer Research, vol. 46, Mar. 1986, pp. 1521-1525.

David W. Robertson et al., "Synthesis of the E and Z Isomers of the Antiestrogen Tamoxifen and its Metabolite, Hydroxytamoxifen, in Tritium-Labeled Form", J. Org. Chem., 1982, vol. 47, No. 12, pp. 2387-2393.

David W. Robertson et al., "Tamoxifen Antiestrogens, a Comparison of the Activity, Pharmacokinetics, and Metabolic Activation of the CIS and Trans Isomers of Tamoxifen" Journal of Steroid Biochemistry, vol. 16, pp. 1-13, (1982).

Fabrice Sauvez et al., "Cutaneously applied 4-hydroxytamoxifen is not carcinogenic in female rats", Carcinogenesis vol. 20, No. 5, pp. 843-850 1999.

Ashini L. Wijayaratne et al., "Comparative Analyses of Mechanistic Differences Among Antiestrogens", Endocrinology, vol. 140, No. 2, pp. 5828-5840.

"First results from the International Breast Cancer Intervention Study (IBIS-I): a randomized prevention trial", The Lancet, vol. 360, Sep. 14, 2002, pp. 817-824.

Carsten Schlüter et al. "The Cell Proliferation-associated Antigen of Antibody Ki-67: A Very Large, Ubiquitous Nuclear Protein with Numerous Repeated Elements, Representing a New Kind of Cell Cycle-maintaining Proteins", The Journal of Cell Biology, vol. 123, 1993, pp. 513-522.

Debra J. Bevitt et al., "New Monoclonal Antibodies to Oestrogen and Progesterone Receptors Effective for Paraffin Section Immunohistochemistry", Journal of Pathology, vol. 183, (1997) pp. 228-232.

Lawrence H. Block Ph.D., Epidermal and Transdermal Drug Delivery, Medicated Topicals, Chapter 44, pp. 836-857.

Corinne Charlier et al., "Tamoxifen and its Active Metabolite Inhibit Growth of Estrogen Receptor-Negative MDA-MB-435 Cells", Biochemical Pharmacology, vol. 49, No. 3, pp. 351-358, 1995.

Ian S. Fentiman, "Tamoxifen and Mastalgia an Emerging Indication", Drugs 32 477-480 (1986), pp. 477-480.

Johannes Gerdes et al., "Cell Cycle Analysis of a Cell Proliferation-Associated Human Nuclear Antigen Defined by the Monoclonal Antibody Ki-67[1]", The Journal of Immunology, vol. 133, No. 4, Oct. 1984, pp. 1710-1715.

J. Girault et al., "Quantitative Measurement of 4-Hydroxy Tamoxifen in Human Plasma and Mammary Tumours by Combined Gas Chromatography/Negative Chemical Ionization Mass Spectrometry", Biological Mass Spectrometry, vol. 22, (1993) pp. 395-402.

Trisha Gura, "Cancer Models: Systems for Identifying New Drugs Are Often Faulty", Science, vol. 278, Nov. 7, 1997, pp. 1041-1042.

Stanley G. Korenman et al., "Estradiol Radioimmunoassay Without Chromatography: Procedure, Validation and Normal Values", J. Clin. Endocrinol. Metab. 38:718-720 (1974).

Catherine Malet et al., "Effect of 4-hydroxytamoxifen isomers on growth and ultrastructural aspects of noram human breast epithelial (HBE) cells in culture", Journal of Steroid Biochemistry & Molecular Biology 82, (2002) pp. 289-296.

Catherine S. Murphy et al., "Structure-Function Relationships of Hydroxylated Metabolites of Tamoxifen that Control the Proliferation of Estrogen-Responsive T47D Breast Cancer Cells In Vitro", Molecular Pharmacology, vol. 38, No. 5, (1990) pp. 737-743.

Mona Nemani et al., "Activation of the human homologue of the *Drosophila sina* gene in apoptosis and tumor suppression", Proc. Natl. Acad. Sci. USA, vol. 93, pp. 9039-9042, Aug. 1996.

Y. Nomura et al., "Effects of antiestrogens and medroxyprogesterone acetate on the clonogenic growth of tamoxifen-sensitve and resistant human breast cancer cells", Japanese Journal of Cancer Chemotherapy, 12(4), pp. 844-850 (1985).

Naushin H. Waseem et al., Monoclonal Antibody Analysis of the Proliferating Cell Nuclear Antigen (PCNA) Structural conservation and the detection of a nucleolar form, Journal of Cell Science, 96, 121-129 (1990).

International Search Report issued on May 13, 2004 in application No. PCT/EP2003/15029.

Pierre Mauvais-Jarvis et al., "trans-4-Hydroxytamoxifen Concentration and Metabolism after Local Percutaneous Administration to Human Breast", Cancer Research, vol. 46, Mar. 1986, pp. 1521-1525.

I. Simony-Lafontaine et al., "Neoadjuvant Percutaneous-4-Hydroxytamoxifen Decreases Breast Cancer Cell Proliferation: A Prospective Randomizediimage Analysis Study", Analytical Cellular Pathology, vol. 25, No. 5-6 2003, pp. 258-259, XP009030125.

Brisson, J., et al., Tamoxifen and Mammographic Breast Densities, Cancer Epidemiology, Biomarkers & Prevention, vol. 9, pp. 911-915 (2000).

"High Breast Density a Risk Factor", pp. 1-4, http://www.breastcancer.org/research_genetics_091902_pf.html (Aug. 11, 2005).

Pujol, H., et al., "Phase I Study of percutaneous 4-hydroxy-tamoxifen with analyses of 4-hydroxy-tamoxifen concentrations in breast cancer and normal breast tissue", Cancer Chemother Pharmacol, vol. 36, pp. 493-498 (1995).

Friend et al., "Simple Alkyl Esters as Skin Permeation Enhancers," *J. of Controlled Release*, 9(1):33-41 (Jun. 1989).

Ruland et al., "Influence of Various Penetration Enhancers on the In Vitro Permeation of Amino Acids Across Hairless Mouse Skin," *International Journal of Pharmaceutics*, 85(1-3):7-17 (Sep. 1992).

Santoyo et al., "Penetration Enhancer Effects on the In Vitro Percutaneous Absorption of Piroxicam Through Rat Skin," *Intl. J. of Pharmaceutics*, 117:219-224 (1995).

Mauvais-Jarvis, "Mastodynia and Fibrocystic Disease," *Current Therapy in Endocrinology and Metabolism*, 3:280-283 (1980).

Mauvais-Jarvis, "Hormal Therapy of Benign Breast Disease," *Senologie et Pathologie Mammaire*, 4ème Congrès International, Paris Sep. 1-4, 1986, pp. 128-132.

Mauvais-Jarvis, "Le Traitement Hormonal des Mastopathies Bènignes," *Bull. Cancer*, 78 :365-371 (1991).

Nishino et al., "Effects of Tamoxifen on Hepatic Fat Content and the Development of Hepatic Steatosis in Patents with Breast Cancer, High Frequency of Involvement and Rapid Reversal After Completion of Tamoxifen Thereapy," *AJR*, 180, Jan. 2003, pp. 129-134.

Shushan et al., "Ovarian cysts in premenopausal and postmenopausal tamoxifen-treated women with breast cancer," *Am. J. Obstet. Gynecol.*, Jan. 1996, pp. 141-144.

Office Action issued May 5, 2006 by the Examiner in U.S. Appl. No. 10/734,638 (US 2005/0031695).

Office Action issued Jan. 6, 2009 by the Examiner in U.S. Appl. No. 10/734,638 (US 2005/0031695).

Office Action issued Oct. 2, 2006 by the Examiner in U.S. Appl. No. 10/734,638 (US 2005/0031695).

Office Action issued Jan. 16, 2007 by the Examiner in U.S. Appl. No. 10/734,638 (US 2005/0031695).

Office Action issued Mar. 13, 2007 by the Examiner in U.S. Appl. No. 10/734,638 (US 2005/0031695).

Office Action issued Dec. 11, 2007 by the Examiner in U.S. Appl. No. 10/734,638 (US 2005/0031695).

Notice of Allowance issued Jun. 13, 2008 by the Examiner in U.S. Appl. No. 10/734,638 (US 2005/0031695).

Office Action issued Aug. 4, 2009 by the Examiner in U.S. Appl. No. 10/734,640 (US 2005/0032909).

Office Action issued Dec. 16, 2008 by the Examiner in U.S. Appl. No. 10/734,640 (US 2005/0032909).

Office Action issued May 29, 2008 by the Examiner in U.S. Appl. No. 10/734,640 (US 2005/0032909).

Office Action issued Aug. 23, 2007 by the Examiner in U.S. Appl. No. 10/734,640 (US 2005/0032909).

Office Action issued Mar. 12, 2007 by the Examiner in U.S. Appl. No. 10/734,640 (US 2005/0032909).

Notice of Allowance issued Dec. 8, 2008 by the Examiner in U.S. Appl. No. 10/734,644 (US 7,485,623).

Office Action issued Oct. 4, 2007 by the Examiner in U.S. Appl. No. 10/734,644 (US 7,485,623).

Office Action issued Apr. 10, 2007 by the Examiner in U.S. Appl. No. 10/734,644 (US 7,485,623).

Advisory Action issued Jul. 7, 2006 by the Examiner in U.S. Appl. No. 10/734,644 (US 7,485,623).

Office Action issued Feb. 24, 2006 by the Examiner in U.S. Appl. No. 10/734,644 (US 7,485,623).

Office Action issued Aug. 23, 2005 by the Examiner in U.S. Appl. No. 10/734,644 (US 7,485,623).

Notice of Allowance issued Nov. 7, 2008 by the Examiner in U.S. Appl. No. 10/805,528 (US 7,507,769).

Office Action issued Feb. 9, 2007 by the Examiner in U.S. Appl. No. 10/805,528 (US 7,507,769).

Office Action issued Jul. 17, 2006 by the Examiner in U.S. Appl. No. 10/805,528 (US 7,507,769).

Office Action issued Nov. 2, 2005 by the Examiner in U.S. Appl. No. 10/805,528 (US 7,507,769).

Advisory Action issued May 19, 2009 by the Examiner in U.S. Appl. No. 10/858,399 (US 2005/0032910).

Office Action issued Feb. 5, 2009 by the Examiner in U.S. Appl. No. 10/858,399 (US 2005/0032910).

Office Action issued Jun. 18, 2008 by the Examiner in U.S. Appl. No. 10/858,399 (US 2005/0032910).

Office Action issued Nov. 1, 2007 by the Examiner in U.S. Appl. No. 10/858,399 (US 2005/0032910).

Office Action issued on Apr. 9, 2010 by the Examiner in U.S. Appl. No. 11/249,122 (US 2006/0105041).

Notice of Allowance issued on Dec. 22, 2009 by the Examiner in U.S. Appl. No. 10/734,638 (US 7,704,516).

Office Action issued on Nov. 12, 2009 by the Examiner in U.S. Appl. No. 10/734,638 (US 7,704,516).

Office Action issued on Sep. 17, 2010 by the Examiner in U.S. Appl. No. 12/397,487 (US 2005/0209340).

Notice of Allowance issued on Jan. 26, 2011 by the Examiner in U.S. Appl. No. 11/009,390 (US 7,968,532).

Office Action issued on Jul. 18, 2011 by the Examiner in U.S. Appl. No. 10/805,530 (US 2005/0208139).

Office Action issued on Feb. 2, 2011 by the Examiner U.S. Appl. No. 12/397,487 (US 2009/0203796).

Notice of Allowance issued on Feb. 2, 2011 by the Examiner U.S. Appl. No. 12/397,487 (US 2009/0203796).

Office Action issued on Jul. 12, 2012 by the Examiner in U.S. Appl. No. 10/805,530 (US 2005/0208139).

Office Action issued on Oct. 22, 2012 by the Examiner in U.S. Appl. No. 11/249,122 (US 2006/0105041).

Office Action issued on May 18, 2012 by the Examiner in U.S. Appl. No. 11/249,122 (US 2006/0105041).

FIGURE 1: Representation of Tamoxifen Metabolism
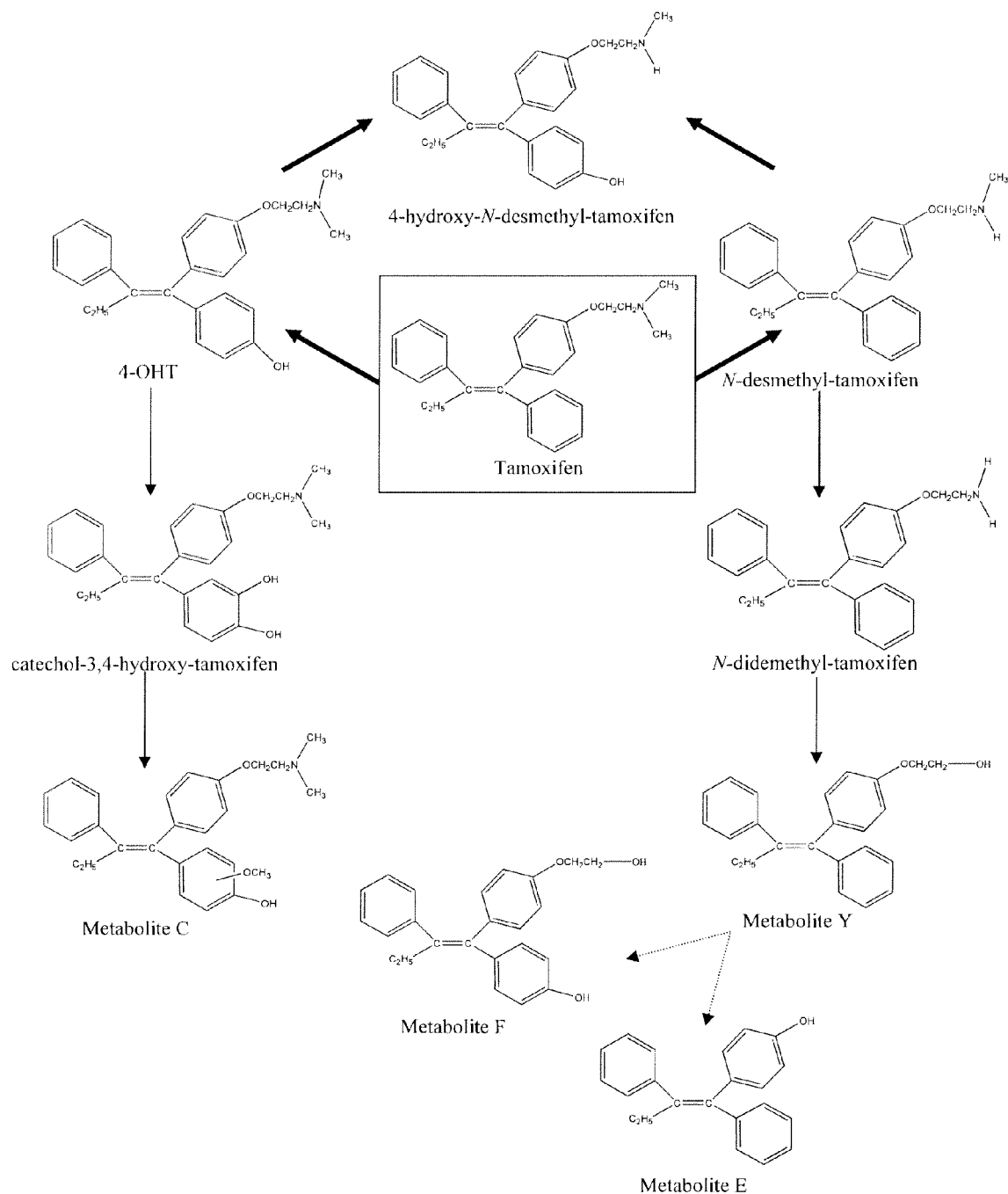

Figure 2: Mean ± SD Plasma Concentration of 4-hydroxy tamoxifen in Healthy Women Following Last Cutaneous Administration (Day 25 of the Second Cycle)
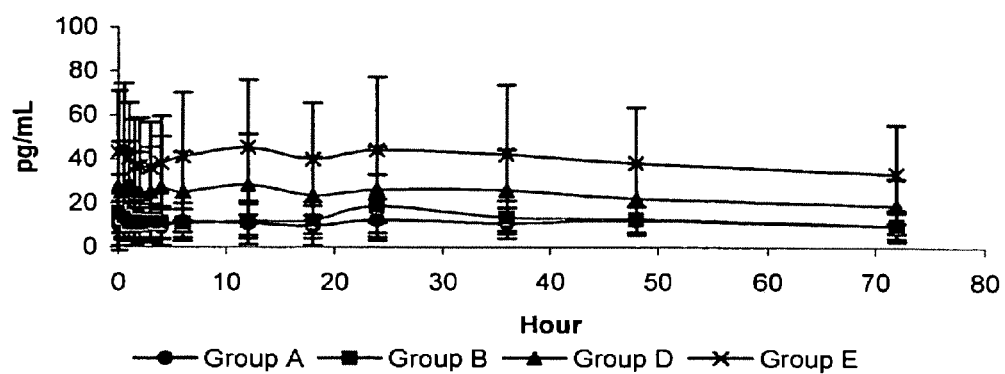

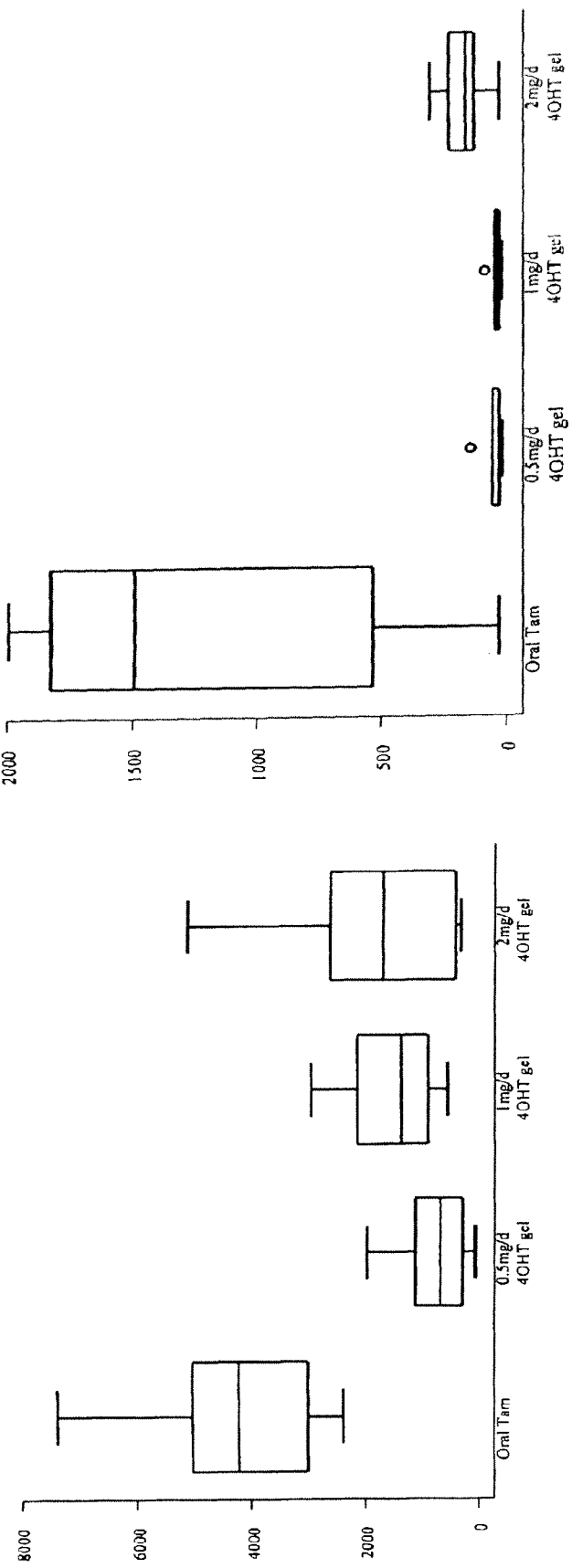

PREVENTION AND TREATMENT OF BREAST CANCER WITH 4-HYDROXY TAMOXIFEN

BACKGROUND OF THE INVENTION

The present invention relates to the treatment and prevention of breast cancer with 4-hydroxy tamoxifen (4-OHT).

Breast cancer constitutes a significant health problem for women in the United States and throughout the world. Despite advances in detection and treatment of the disease, breast cancer remains the second leading cause of cancer-related deaths in women, affecting more than 180,000 women in the United States alone each year. For women in North America, the life-time odds of getting breast cancer are one in eight.

No universally successful method for preventing or treating breast cancer currently exists. Management of the disease relies on a combination of early diagnosis (through routine breast screening procedures) and aggressive treatment, which may include one or more of a variety of treatments such as surgery, radiotherapy, chemotherapy and hormone therapy. These therapies are dangerous, toxic, costly, and often ineffective, especially in the treatment of metastatic disease.

The most commonly prescribed hormonal medication for breast cancer is tamoxifen. It works by blocking the effects of estrogen, which promotes the growth of breast cancer cells. As a treatment for breast cancer, tamoxifen slows or stops the growth of cancer cells that are already present in the body, and helps prevent recurrences and the development of new cancers. Taking tamoxifen for 5 years reduces the risk of recurrence by about half in patients with estrogen receptor positive cancers. Tamoxifen also decreases the incidence of breast cancer involving the opposite breast (contralateral) in both premenopausal and postmenopausal women. Moreover, tamoxifen has recently been found to reduce the incidence of breast cancer in women at high risk of developing this disease.

In spite of its benefits, tamoxifen has significant drawbacks. Its action potentially impacts on every estrogen receptor bearing cell in the body, and, as both an agonist and antagonist, tamoxifen provokes a wide range of systemic effects. These effects increase the risk of endometrial cancer, endometrial hyperplasia and polyps, deep vein thrombosis and pulmonary embolism, changes in liver enzyme levels, and ocular toxicities, including cataracts. Additionally, patients treated with oral tamoxifen reported having hot flashes, vaginal discharge, depression, amenorrhea, and nausea (Ibis, 2002; Fentiman 1986, 1988, 1989).

Due to tamoxifen's drawbacks, some cancer researchers have proposed using 4-hydroxy tamoxifen, a metabolite of tamoxifen, for breast cancer. In in vitro studies, 4-hydroxy tamoxifen inhibits the growth of both normal and cancerous breast cells (Nomura, 1985; Malet, 1988, 2002; Charlier, 1995). Additionally, transdermally delivered 4-hydroxy tamoxifen exhibits an anti-tumor effect on human breast tumors grown subcutaneously in mice (U.S. Pat. No. 5,904,930).

Limited experiments in humans have shown that percutaneously administered 4-hydroxy tamoxifen can concentrate in local breast tumors, with very little systemic distribution (Mauvais-Jarvis, 1986). However, the most extended reported study of this sort, in which patients were treated for three weeks, showed that breast tissue concentrations of 4-hydroxy tamoxifen administered percutaneously remained lower than those observed after oral tamoxifen treatment (Pujol, 1995). Accordingly, the researchers concluded that they could not propose percutaneous 4-hydroxy tamoxifen as an alternative tamoxifen treatment.

Importantly, none of the reported studies regarding 4-hydroxy tamoxifen in humans has evaluated an anti-tumor effect. This failure leaves wide open the most important question—whether percutaneously administered 4-hydroxy tamoxifen actually exerts any effect on breast cancer in humans. Therefore, a strong need still exists for breast cancer treatments and prophylactics that provoke few systemic side effects.

SUMMARY OF THE INVENTION

The present invention includes a method of treating breast cancer by administering 4-hydroxy tamoxifen. This treatment approach, preferably implemented topically, effectively reduces tumor tissue proliferation and results in lower plasma drug levels than oral tamoxifen.

The present invention also includes a method of preventing breast cancer by administering 4-hydroxy tamoxifen. As with the treatment approach, the prophylactic approach also is preferably implemented topically.

For purposes of prophylaxis or treatment, 4-hydroxy tamoxifen may be administered by any means that delivers it to estrogen receptor-bearing cells in vivo. As noted, it is preferable that the administration be done percutaneously (topically), to avoid the first-pass effect and related liver metabolism of the 4-hydroxy tamoxifen. For percutaneous administration, 4-hydroxy tamoxifen may be applied to any skin surface. Application to the breasts is advantageous because 4-hydroxy tamoxifen tends to concentrate in local subcutaneous tissues with estrogen receptors when administered percutaneously.

A broad range of topical formulations are suitable for performing the invention, but hydroalcoholic solutions and hydroalcoholic gels are preferred. The concentration of 4-hydroxy tamoxifen in these formulations may vary, but a dose should result in local 4-hydroxy tamoxifen tissue concentrations that effectively oppose estrogenic driven effects.

BRIEF DESCRIPTION OF THE FIGURES

FIG. 1 illustrates the metabolism of tamoxifen.

FIG. 2 illustrates the mean plasma concentration of 4-hydroxy tamoxifen in healthy women following cutaneous administration.

FIG. 3 illustrates the concentration of 4-hydroxy tamoxifen in tissues, according to mode of administration and dosage. Panel A shows the concentration of 4-hydroxy tamoxifen in tumor tissues. Panel B shows the concentration of 4-hydroxy tamoxifen in plasma. The top and bottom of each box represent the $75^{th}$ and $25^{th}$ percentiles, respectively. The horizontal line within the boxes represents the $50^{th}$ (meridian) and the end of each "whisker" the $10^{th}$ and $90^{th}$ percentiles.

DETAILED DESCRIPTION OF THE PREFERRED EMBODIMENTS

An important aspect of the present invention is the surprising discovery that 4-hydroxy tamoxifen, when administered percutaneously, is effective not only in treating but also in preventing breast cancer. Moreover, percutaneously administered 4-hydroxy tamoxifen results in lower plasma levels of the drug than the standard dose of oral tamoxifen, which translates to fewer adverse side effects. Accordingly, percutaneous 4-hydroxy tamoxifen is an alternative to tamoxifen for both treatment and prophylaxis in this context.

The inventors have performed the first study to demonstrate that 4-hydroxy tamoxifen reduces breast tumor proliferation in vivo in humans (see Example 4, below). In brief, they administered 4-hydroxy tamoxifen gel percutaneously to human patients diagnosed with estrogen receptor positive breast cancer. After only 2-3 weeks of administration, the inventors observed dose-related reductions in tumor tissue proliferation indexes, with the highest dose (2.0 mg/day) showing approximate equivalence to a standard dose of oral tamoxifen. The tumor tissue proliferation indexes evaluated were Ki67 (Gerdes 1984; Schluter 1993) and Proliferating Cell Nuclear Antigen (PCNA) (Waseem, 1990). Although percutaneous 4-hydroxy tamoxifen gel and oral tamoxifen were equivalent in reducing tumor tissue proliferation, 4-hydroxy tamoxifen plasma levels were consistently lower in patients receiving 4-hydroxy tamoxifen gel.

The compound 4-hydroxy tamoxifen, or 1-[4-(2-N-dimethylaminoethoxy)phenyl]-1-(4-hydroxyphenyl)-2-phenyl-but-1-ene, constitutes an active metabolite of the well characterized anti-estrogen compound, tamoxifen. Due to the presence of a double bond between two carbon atoms, 4-hydroxy tamoxifen exists in two stereoisomeric forms. According to the medical and biochemical literature, isomeric forms of 4-hydroxy tamoxifen are commonly designated as cis and trans isomers. From a purely chemical perspective, however, this designation is not strictly accurate because each double bonded carbon atom does not contain an identical chemical group. Therefore, it is more appropriate to refer to the isomers as E (the so-called cis form) and Z (the so-called trans form) configurations. Both the E and Z isomers of 4-hydroxy tamoxifen, either alone or in combination, are useful according to the present invention. The Z isomer is preferred, however, because it is more active than the E isomer.

4-Hydroxy tamoxifen acts as a selective estrogen receptor modulator (SERM) that exhibits tissue-specificity for estrogen receptive tissues. In breast tissue, it functions as an estrogen antagonist. Studies have shown that 4-hydroxy tamoxifen can regulate the transcriptional activity of estrogen-related receptors, which may contribute to its tissue-specific activity. In vitro, 4-hydroxy tamoxifen exhibits more potency than tamoxifen, as measured by binding affinity to estrogen receptors, or ERs, and a binding affinity similar to estradiol for estrogen receptors (Robertson et al., 1982; Kuiper et al., 1997). Z-4-hydroxy tamoxifen inhibits the growth in culture of normal human epithelial breast cells 100 fold more than Z-tamoxifen (Malet et al., 1988).

Although 4-hydroxy tamoxifen is a tamoxifen metabolite, its usefulness for breast cancer is not presaged by previous experience with tamoxifen itself. Tamoxifen is extensively metabolized in humans, as shown in FIG. 1. Thus, its action in vivo is the net result of individual actions by the parent compound and its metabolite compounds competing for the occupation of receptors within target tissues. For example, see Jordan, 1982. Each of these compounds manifests different and unpredictable biological activities in different cells, determined in part by each compound's individual effect on estrogen receptor conformation. That is, estrogen receptor binding of each compound generates a unique receptor-ligand conformation that recruits different cofactors, and results in varying pharmacologies for the different compounds (Wijayaratne et al., 1999; Giambiagi et al., 1988).

Several examples of these varying effects have been documented. For instance, tamoxifen but not 4-hydroxy tamoxifen is a potent rat liver carcinogen. (Carthew et al., 2001; Sauvez et al., 1999). Additionally, tamoxifen but not 4-hydroxy tamoxifen reportedly initiates apoptosis in p53(−) normal human mammary epithelial cells (Dietze et al., 2001). By contrast, 4-hydroxy tamoxifen exhibits a significant inhibitory effect on estrone sulphatase activity in mammary cancer cell lines, while tamoxifen has little or no effect in this regard (Chemite et al., 1993).

Previous studies with 4-hydroxy tamoxifen also did not predict its effectiveness for breast cancer treatment and prevention. The ability of any drug to inhibit tumor cell growth in vitro or in a xenograft assay is a crude indicator of how the drug might act in humans (Gura, 1997). Cell culture, an artificial environment, provides no information regarding how a drug acts in a complete biological system, and animals often do not process drugs the same way as humans. Moreover, previous human studies with 4-hydroxy tamoxifen only evaluated drug delivery, and provided no information regarding the drug's effect on breast tumors. By contrast, experiments performed by the present inventors have surprisingly shown that 4-hydroxy tamoxifen, administered percutaneously, causes dose-related reductions in tumor tissue proliferation indexes.

Methods for preparing 4-hydroxy tamoxifen are well known. For example, U.S. Pat. No. 4,919,937 describes a synthesis, derived from Robertson and Katzenellenbogen, 1982, that occurs in stages:

Stage 1—Reaction between 4-(β-dimethylaminoethoxy)-α-ethyldeoxybenzoin and p-(2-tetrahydropyranyloxy) phenylmagnesium bromide;

Stage 2—Separately from stage 1, formation of 1-(4-hydroxyphenyl)-2-phenyl-1-butanone by hydroxylation of 1,2-diphenyl-1-butanone;

Stage 3—Reaction between the products of stages 1 and 2 to form 1-(4-dimethylaminoethoxyphenyl)-1-[p-2-tetrahydropyranyloxy)phenyl]-2-phenylbutan-1-ol;

Stage 4—Dehydration with methanol/hydrochloric acid produces 1-[p-(β-dimethylaminoethoxy)phenyl]-Z-1-(p-hydroxyphenyl)-2-pheny-1-but-1-ene=4-OH-tamoxifen, a mixture of E and Z isomers;

Stage 5—Separation of the E and Z isomers by chromatography and crystallization to constant specific activity.

According to the present invention, 4-hydroxy tamoxifen may be administered to a patient diagnosed with breast cancer. The cancer preferably will be estrogen receptor positive, as it is believed that 4-hydroxy tamoxifen primarily exerts its effect by acting on estrogen receptors. Additionally, it is preferred that the breast cancer be localized to the breast. For example, a primary breast tumor and/or a metastatic tumor solely located in the breast may be treated by topical administration. Breast cancer tumors at other locations that are accessible to topically administered 4-hydroxy tamoxifen also may be treated in this manner, however.

The present invention also contemplates administration of 4-hydroxy tamoxifen prophylactically, to a patient at increased risk for developing breast cancer. Many risk factors for breast cancer are well established. For instance, family history of breast cancer, personal history of breast cancer, previous breast biopsy detection of proliferative breast disease such as atypical hyperplasia, and previous breast irradiation all place a patient at an elevated risk for developing breast cancer. Particular genetic risk factors include BRCA1, BRCA2, ATM, CHEK-2 and p53 mutations. Certain lifestyle-related risk factors for women include delayed childbirth until after age 30, long-term use of oral contraceptives, and long-term use of hormone replacement therapy. A skilled medical practitioner can evaluate these and other risk factors to determine whether a patient will benefit from prophylactic use of 4-hydroxy tamoxifen. In making such an assessment, a practitioner may employ the Gail model.

4-Hydroxy tamoxifen is particularly useful for preventing breast cancer in pre-menopausal women. In this population, an anti-estrogen must compete with high amounts of circulating estrogen to occupy estrogen receptors. Because 4-hydroxy tamoxifen has 100 fold more affinity for estrogen receptors than tamoxifen, it is better able to compete for the receptors at low doses. The ability to use a low dose holds particular importance in a prophylactic context, where a patient's exposure to the drug is long-term and side effects are less tolerable.

Pursuant to the present invention, 4-hydroxy tamoxifen may be administered in any dosage form and via any system that delivers the active compound to breast and/or tumor estrogen receptors in vivo. Preferably, the 4-hydroxy tamoxifen is delivered by "percutaneous administration," a phrase that denotes any mode of delivering a drug from the surface of a patient's skin, through the stratum corneum, epidermis, and dermis layers, and into the microcirculation. This is typically accomplished by diffusion down a concentration gradient. The diffusion may occur via intracellular penetration (through the cells), intercellular penetration (between the cells), transappendageal penetration (through the hair follicles, sweat, and sebaceous glands), or any combination of these.

Percutaneous administration of 4-hydroxy tamoxifen offers several advantages. First, it avoids the hepatic metabolism that occurs subsequent to oral administration (Mauvais-Jarvis et al., 1986). Second, percutaneous administration significantly reduces systemic drug exposure, and the attendant risks from non-specifically activating estrogen receptors throughout the body; this, because topical 4-hydroxy tamoxifen is absorbed primarily into local tissues. In particular, when 4-hydroxy tamoxifen is percutaneously applied to breasts, high concentrations accumulate in the breast tissue, presumably due to many estrogen receptors therein, without creating a high plasma concentration (Mauvais-Jarvis et al., supra). Pursuant to the present invention, therefore, 4-hydroxy tamoxifen may be applied to any skin surface, but preferably to one or both breasts.

Although the invention is not constrained to any particular theory, clinically significant side effects of anti-estrogen agents occur when the agents displace estradiol in non-target tissues. Because 4-hydroxy tamoxifen and estradiol have similar binding affinities for estrogen receptors, a competition between them for receptor binding would be approximately equal when the concentration of each compound approximates that of the other. If the 4-hydroxy tamoxifen concentration exceeds the estradiol concentration, the former will be bound preferentially to the estrogen receptors, and vice versa.

Accordingly, doses of 4-hydroxy tamoxifen that result in plasma concentrations less than about 80 pg/mL, or the mean estradiol concentration in normal premenopausal women, are preferred. More preferably, doses of 4-hydroxy tamoxifen will result in plasma concentrations less than about 50 pg/mL. The daily doses to be administered can initially be estimated based upon the absorption coefficients of 4-hydroxy tamoxifen, the breast tissue concentration that is desired, and the plasma concentration that should not be exceeded. Of course, the initial dose may be optimized in each patient, depending on individual responses.

As noted above, by targeting 4-hydroxy tamoxifen to breast tissue, high concentrations can be achieved in that tissue without simultaneously raising 4-hydroxy tamoxifen plasma levels to a point where significant systemic competition for estradiol receptors occurs. At a percutaneous dose of 1 mg/breast/day, 4-hydroxy tamoxifen concentration in breast tissue exceeds normal estradiol concentrations in breast tissue by a factor of 4. (Barrat et al., 1990; Pujol et al., supra). Moreover, 4-hydroxy tamoxifen applied in this manner reaches concentrations in breast tissue that are an order of magnitude higher than concentrations in plasma, i.e., 10:1. By contrast, the breast tissue to plasma ratio of 4-hydroxy tamoxifen following oral administration of tamoxifen is about 5:1.

In a percutaneous formulation, doses on the order of 0.25-2.0 mg/breast/day of 4-hydroxy tamoxifen should achieve the desired result, with doses of about 0.5-1.0 mg/breast/day being preferred. In particular embodiments, the dosage is about 0.5, 0.75 or 1.0 mg/breast/day of 4-hydroxy tamoxifen.

Percutaneous administration can be accomplished mainly in two different ways: (i) by mixing a therapeutically active compound or its non-toxic pharmaceutically acceptable salt with suitable pharmaceutical carriers and, optionally, penetration enhancers to form ointments, emulsions, lotions, solutions, creams, gels or the like, where an amount of said preparation is applied onto a certain area of the skin, or (ii) by incorporating the therapeutically active substance into patches or transdermal delivery systems according to known technology.

The effectiveness of percutaneous drug administration depends on many factors, including drug concentration, surface area of application, time and duration of application, skin hydration, physicochemical properties of the drug, and partitioning of the drug between the formulation and the skin. Drug formulations intended for percutaneous use take advantage of these factors to achieve optimal delivery. Such formulations often comprise penetration enhancers that improve percutaneous absorption by reducing the resistance of the stratum corneum by reversibly altering its physiochemical properties, changing hydration in the stratum corneum, acting as co-solvent, or changing the organization of lipids and proteins in the intercellular spaces. Such enhancers of percutaneous absorption include surfactants, DMSO, alcohol, acetone, propyleneglycol, polyethylene glycol, fatty acids or fatty alcohols and their derivatives, hydroxyacids, pyrrolidones, urea, essential oils, and mixtures thereof. In addition to chemical enhancers, physical methods can increase percutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics.

The many factors and methods relating to percutaneous drug delivery are reviewed in REMINGTON: THE SCIENCE AND PRACTICE OF PHARMACY, Alfonso R. Gennaro (Lippincott Williams & Wilkins, 2000), at pages 836-58, and in PERCUTANEOUS ABSORPTION: DRUGS COSMETICS MECHANISMS METHODOLOGY, Bronaugh and Maibach (Marcel Dekker, 1999). As these publications evidence, those in the pharmaceutical field can manipulate the various factors and methods to achieve efficacious percutaneous delivery.

4-Hydroxy tamoxifen is a large and very lipophilic molecule; hence, without assistance from penetration enhancers it poorly penetrates the skin. Accordingly, formulations of 4-hydroxy tamoxifen used in the present invention preferably comprise one or more penetration enhancers. Alcohols are preferred enhancers because 4-hydroxy tamoxifen is soluble in alcohol. Isopropyl myristate also is a preferred enhancer.

For percutaneous administration, 4-hydroxy tamoxifen may be delivered in an ointment, cream, gel, emulsion (lotion), powder, oil or similar formulation. To this end, the formulation may comprise customary excipient additives, including vegetable oils such as almond oil, olive oil, peach kernel oil, groundnut oil, castor oil and the like, animal oils, DMSO, fat and fat-like substances, lanolin lipoids, phosphatides, hydrocarbons such as paraffins, petroleum jelly, waxes, detergent emulsifying agents, lecithin, alcohols, carotin, polyols or polyglycols such as glycerol (or glycerine), glycerol ethers, glycols, glycol ethers, polyethylene glycol, polypropylene glycol, non-volatile fatty alcohols, acids, esters, volatile alcoholic compounds, urea, talc, cellulose derivatives, coloring agents, antioxidants and preservatives.

According to the present invention, 4-hydroxy tamoxifen also may be delivered via a transdermal patch. In one embodiment, the patch comprises a reservoir for the 4-hydroxy tamoxifen formula. The patch may comprise (a) a solution-impermeable backing foil, (b) a layer-like element having a cavity, (c) a microporous or semi-permeable membrane, (d) a self-adhesive layer, and (e) optionally, a removable backing film. The layer-like element having a cavity may be formed by the backing foil and the membrane. Alternatively, the patch may comprise (a) a solution-impermeable backing foil, (b) an open-pored foam, a closed-pore foam, a tissue-like layer or a fibrous web-like layer as reservoir, (c) if the layer according to (b) is not self-adhesive, a self-adhesive layer, and (d) optionally a removable backing film.

In preferred embodiments of the invention, 4-hydroxy tamoxifen is formulated in a hydroalcoholic gel. The amount of 4-hydroxy tamoxifen in such a gel may range from about 0.001 to about 1.0 gram of 4-hydroxy tamoxifen per 100 grams of gel. Preferably, it ranges from about 0.01 to about 0.1 gram of 4-hydroxy tamoxifen per 100 grams of gel.

It is also preferred that 4-hydroxy tamoxifen formulations comprise one or more fatty acid esters as a penetration enhancer. One highly preferred example of a fatty acid ester penetration enhancer is isopropyl myristate. When isopropyl myristate is used in a gel, the amount may range from about 0.1 to about 5.0 grams per 100 grams of gel. Preferably, the amount of isopropyl myristate ranges from about 0.5 to about 2.0 grams per 100 grams of gel.

4-Hydroxy tamoxifen formulations of the invention generally will comprise one or more nonaqueous vehicles. These vehicles should be capable of dissolving both 4-hydroxy tamoxifen and any penetration enhancer used. They also should have a low boiling point, preferably less than 100° C. at atmospheric pressure, to permit rapid evaporation upon contact with the skin. Examples of suitable non-aqueous vehicles include ethanol, isopropanol and ethyl acetate. Ethanol and isopropanol are preferred. In particular, ethanol effectively contributes to the percutaneous absorption of 4-hydroxy tamoxifen by rapidly evaporating upon contact with skin. The amount of nonaqueous vehicle in a gel formulation generally ranges between 54% and 85% by weight, and preferably between 65% and 75.

Formulations also may comprise an aqueous vehicle, which permits solubilization of any hydrophilic molecules in a formulation, and also promotes diffusion of lipophilic molecules from the formulation to the skin. An aqueous vehicle also can regulate pH. Aqueous vehicles include alkalinizing and basic buffer solutions, including phosphate buffered solutions (e.g., dibasic or monobasic sodium phosphate), citrate buffered solutions (e.g., sodium citrate or potassium citrate) and simply purified water. The amount of an aqueous vehicle preferably ranges between 15% and 45% by weight of a gel formulation, and more preferably between 25% and 35%.

Additionally, 4-hydroxy tamoxifen formulations may comprise one or more gelling agents to increase the viscosity of a formulation and/or to function as a solubilizing agent. Depending on the gelling agent's nature, it may constitute between 0.1% and 20% by weight of a formulation, preferably between 0.5% and 10%, and still more preferably between 1% and 5%. Preferred gelling agents include carbomers, cellulose derivatives, poloxamers and poloxamines. More particularly, preferred gelling agents are chitosan, dextran, pectins, natural gum and cellulose derivatives such as ethyl cellulose, hydroxypropyl cellulose, hydroxyethyl cellulose, hydroxypropyl methyl cellulose (HPMC), carboxymethyl cellulose (CMC), and the like. One highly preferred gelling agent is hydroxypropyl cellulose.

When a formulation comprises a gelling agent, in particular a non-preneutralized acrylic polymer, it may advantageously also comprise a neutralizing agent. The neutralizing agent/gelling agent ratio preferably is between 10:1 and 0.1:1, more preferably between 7:1 and 0.5:1, and still more preferably between 4:1 and 1:1. A neutralizing agent should form, in the presence of the polymer, salts that are soluble in the vehicle. A neutralizing agent also should permit optimum swelling of polymer chains during neutralization of charges and formation of polymer salts. Useful neutralizing agents include sodium hydroxide, ammonium hydroxide, potassium hydroxide, arginine, aminomethylpropanol and tromethamine. Those skilled in the art will select a neutralizing agent according to the type of gelling agent employed in a formulation. When cellulose derivatives are used as gelling agents, however, no neutralizing agents are required.

Table 1 describes the composition of two highly preferred 4-hydroxy tamoxifen gel formulations.

TABLE 1

Composition of 4-Hydroxy Tamoxifen Gel Formulations

| | Quantity per 100 g of gel | |
| Ingredient | 20 mg 4-OHT Gel | 57 mg 4-OHT Gel |
| --- | --- | --- |
| 4-Hydroxy Tamoxifen | 0.02 g | 0.057 g |
| 95% Ethyl Alcohol, EP | 72 g | 72 g |
| Isopropyl myristate, EP | 1 g | 1 g |
| Hydroxypropylcellulose, EP | 1.5 g | 1.5 g |
| Phosphate Buffer (pH 7, diluted 1:4) | q.s. 100 g | q.s. 100 g |

Reference to the following, illustrative examples will help to provide a more complete understanding of the invention.

EXAMPLE 1

Demonstration of Percutaneous 4-Hydroxy Tamoxifen Delivery

Four patients with breast cancer received [$^3$H]-4-hydroxy tamoxifen in an alcoholic solution applied directly to the breasts at specified intervals between 12 hours to 7 days prior to surgery to excise diseased tissue. After surgery, both the excised tissue and the normal breast tissue surrounding the tumor contained radioactivity (Kuttenn et al., 1985).

In a follow-up study, 9 of 12 patients scheduled for surgical excision of hormone-dependent breast cancer received Z-[$^3$H]-4-hydroxy tamoxifen (80 μci) in a 60% alcoholic solution, and 3 patients received Z-[$^3$H]-tamoxifen (80 μci) for comparison. The patients received [$^3$H]-labeled drug applied directly on the affected breasts at specified intervals ranging from 12 hours to 7 days before surgery to excise diseased tissue. Breast tissue from three regions: the tumor, tissue immediately surrounding the tumor, and normal tissue, was excised and immediately frozen in liquid nitrogen. Additionally, plasma and urine samples were obtained at scheduled intervals and frozen until analysis.

Table 2 shows results from the analyses performed. 4-Hydroxy tamoxifen concentrated predominantly in the cytosolic and nuclear fractions of breast tissue, where estrogen receptors are present. In these intracellular sites, 4-hydroxy tamoxifen remained unmetabolized except for limited isomerization from the Z to the E form. Retention in the breast lasted approximately 4 days in the 4-hydroxy tamoxifen group, but was shorter and far weaker in the tamoxifen group.

TABLE 2

[$^3$H]-4-Hydroxy Tamoxifen and Metabolites Identified in Breast Tumor Tissue Following Percutaneous Administration of Z-[$^3$H]-4-Hydroxy Tamoxifen to the Affected Breast

| Metabolites | % Metabolites in Breast Tissue | | | | |
|---|---|---|---|---|---|
| | 12 hr[1] | 24 hr | 36 hr | Day 4 | Day 7 |
| 4-Hydroxy Tamoxifen | 97 | 94 | 78 | 70 | 65 |
| N-Desmethyl-4-Hydroxy Tamoxifen | 2 | 4 | 14 | 20 | 16 |
| Bisphenol | 1 | 2 | 3 | 8 | 8 |
| N-Desmethyl tamoxifen | | | <1 | <1 | 3-4 |
| Tamoxifen | | | | <1 | 2 |

[1]Time after administration of Z-[$^3$H]-4-hydroxy tamoxifen

The percentage of radioactivity identified as [$^3$H]-4-hydroxy tamoxifen in breast tissue after percutaneous administration decreased slowly over seven days (from 97% to 65%). During this period a progressive isomerization of the Z isomer into the E isomer occurred, with similar percentages observed at day 7 (32% and 33%).

The radioactivity in blood due to [$^3$H]-4-hydroxy tamoxifen increased gradually, with a plateau from days 4 to 6. This contrasts with [$^3$H]-tamoxifen, which rapidly appeared in the blood, plateauing at 2 days. At 36 hours following percutaneous [$^3$H]-4-hydroxy tamoxifen administration, only 0.5% of the radioactivity administered showed in the blood.

In contrast to the near absence of 4-hydroxy tamoxifen metabolism in the breast tissue, marked metabolism occurred in blood. In blood, at 24 hours after administration, 68% of radioactivity represented 4-hydroxy tamoxifen, 18% represented N-desmethyl-4-hydroxy tamoxifen, and 11% represented bisphenol.

Peak urinary elimination occurred at a later time following percutaneous administration of 4-hydroxy tamoxifen compared to percutaneous tamoxifen. Following application of 4-hydroxy tamoxifen, a progressive increase of metabolites, mostly N-desmethyl-4-hydroxy tamoxifen and bisphenol, was observed in the urine.

This example demonstrates that percutaneous application of 4-hydroxy tamoxifen to the breasts results in a substantial and lasting local tissue concentration of the drug, with minimal metabolism, stable and very low plasma concentrations, and slow elimination via the urine.

EXAMPLE 2

Demonstration of the Pharmacokinetics and Pharmacodynamics of Percutaneously Administered 4-OH-Tamoxifen Compared to 20 mg of Oral Tamoxifen This study compared the tissue and plasma concentrations of 4-hydroxy tamoxifen after percutaneous administration via a hydroalcoholic gel with tissue and plasma concentrations of 4-hydroxy tamoxifen after oral administration of tamoxifen (Pujol, 1995).

Thirty-one patients scheduled for breast cancer surgery were randomly assigned to 1 of 5 groups. They received treatment with either oral tamoxifen or percutaneous 4-hydroxy tamoxifen as outlined in Table 3. Treatment was daily and lasted for 3-4 weeks prior to surgery. The study evaluated three different doses of 4-hydroxy tamoxifen (0.5, 1, or 2 mg/day) and two areas of application (either to both breasts or to a large surface of skin including arms, forearms, and shoulders). One group of patients received 20 mg/day (10 mg b.i.d.) of oral tamoxifen (Nolvaldex®).

TABLE 3

Treatment Groups

| Group | N | Drug | Application Site | Dose mg/breast/day | Total Daily Dose (mg/day) |
|---|---|---|---|---|---|
| 1 | 6 | PO tamoxifen | — | — | 20[a] |
| 2 | 6 | 4-OHT gel | both breasts | 0.25 | 0.5 |
| 3 | 5 | 4-OHT gel | both breasts | 0.50 | 1 |
| 4 | 5 | 4-OHT gel | arms, forearms, and shoulders | — | 1 |
| 5 | 6 | 4-OHT gel | arms, forearms, and shoulders | — | 2[b] |

[a]10 mg b.i.d.
[b]divided into 2 daily applications; 1 mg in the morning and 1 mg in the evening The 4-hydroxy tamoxifen gel (20 mg of 4-hydroxy tamoxifen/100 g of hydroalcoholic gel; Besins-International Laboratories) was packaged in a pressurized dose-metering pump that delivered 1.25 g of gel/metered dose (i.e., 0.25 mg of 4-hydroxy tamoxifen/dose).

During surgery; two samples (1 cm³ each) of breast tissue were excised, one tumoral and the other macroscopically normal. They were immediately frozen in liquid nitrogen until assayed. Blood samples were obtained on the day of and the day prior to surgery. All tissue and plasma samples were analyzed for 4-hydroxy tamoxifen concentration by gas chromatograph/mass spectrometry (GC-MS).

Pre and post-treatment blood samples were assayed for complete blood counts (CBC), bilirubin, serum glutamic-pyruvic transaminase (SGPT), serum glutamic-oxaloacetic transaminase (SGOT), alkaline phosphatase, creatinine, estradiol, follicle-stimulating hormone (FSH), luteinizing hormone (LH), sex hormone-binding globulin (SHBG), cholesterol, high-density lipoprotein (HDL), low-density lipoprotein (LDL), triglycerides, fibrinogen, and anti-thrombin III.

Table 4 below summarizes the concentration of 4-hydroxy tamoxifen found in breast tissue and plasma. Normal and tumor breast tissues contained similar concentrations of 4-hydroxy tamoxifen in all five treatment groups. 4-hydroxy tamoxifen concentrated at higher amounts in breast tissue when the gel was applied directly to the breasts, rather than to other large skin surfaces.

TABLE 4

Concentrations of 4-hydroxy tamoxifen

| | | Mean ± SD 4-hydroxy tamoxifen (Range) | | | |
|---|---|---|---|---|---|
| | | Plasma Concentrations (pg/mL) | | Normal Tissue | |
| Group | N | Day Pre-Surgery | Day of Surgery | (pg/g) | Tumor (pg/g) |
| 1 | 6 | 2326 ± 585 (1371-2959)[a] | 2317 ± 1098 (881-4176) | 10215 ± 2151 (5873-11511) | 12453 ± 3751 (9568-18904)[a] |
| 2 | 6 | 0 (0-0)[a] | 17 ± 27 (0[c]-61) | 353 ± 513 (0[d]-1317) | 1447 ± 2673 (0[f]-6889) |
| 3 | 5 | 164 ± 131 (29-279)[b] | 62 ± 71 (28-190) | 1112 ± 1125 (197-2979 | 1877 ± 2472 (345-6211) |
| 4 | 5 | 94 ± 76 (35-201)[b] | 13 ± 29 (0[c]-65) | 140 ± 130 (0[e]-270) | 552 ± 357 (271-1150) |
| 5 | 6 | 78 ± 138 (0[e]-284)[b] | 73 ± 114 (0[c]-244) | 992 ± 2195 (0[d]-5462) | 224 ± 312 (0[d]-799) |

[a] n = 5
[b] n = 4
[c] 4 patients had undetectable levels of 4-hydroxy tamoxifen (LOQ = 20 pg/ml)
[d] 3 patients had undetectable levels of 4-hydroxy tamoxifen
[e] 2 patients had undetectable levels of 4-hydroxy tamoxifen
[f] 1 patient had undetectable levels of 4-hydroxy tamoxifen Side effects did not pose a significant problem. Cutaneous treatment did not cause any local irritation. One woman in Group 2 (0.5 mg/day of 4-hydroxy tamoxifen gel) reported dizzy spells, cystitis, and mild vaginitis occurring on the seventh day of treatment. One woman in Group 1 (oral tamoxifen) reported hot flashes and mild vaginitis on the fifth day of treatment.

No differences existed between the pre- and post treatment blood samples for any of the hematology or serum chemistry evaluations in the patients who received 4-hydroxy tamoxifen gel. However, a statistically significant decrease in antithrombin III and fibrinogen and a statistically significant increase in platelet and lymphocyte counts were observed in the oral tamoxifen group, consistent with the biologic effects of this drug observed in other studies.

EXAMPLE 3

Demonstration of Tolerance and Pharmacokinetics of Percutaneously Administered 4-OH-Tamoxifen in Healthy Women This study demonstrates the tolerance and pharmacokinetics of topically applied 4-hydroxy tamoxifen gel in healthy premenopausal women, aged 18-45. Each participant applied the gel daily for the duration of two menstrual cycles.

Three doses and two gel concentrations were tested, as summarized in Table 5. For Groups A-C, the gel, containing 20 mg of 4-hydroxy tamoxifen/100 g, was dispensed from a pressurized dose-metering pump that delivered 0.25 mg of 4-hydroxy tamoxifen/dose. The study of Group C was suspended because the quantity of gel was too large to be applied to a single breast. Groups D and E received a more concentrated gel that contained almost 3 times as much 4-hydroxy tamoxifen: 57 mg of 4-hydroxy tamoxifen/100 g, or 50 mg of 4-hydroxy tamoxifen/100 mL of gel. This more concentrated gel also was delivered by a dose-metering pump that supplied 0.25 mg of 4-hydroxy tamoxifen/dose.

TABLE 5

Treatment Groups

| Group | N | Dose (mg/day) | Gel Concentration (mg of 4-OHT/g of gel) | Treatment |
|---|---|---|---|---|
| A | 12 | 0.5 | 20 mg/100 g | 1 metered dose/breast/day |
| B | 8 | 1 | 20 mg/100 g | 2 metered doses/breast/day |
| C | 2 | 2 | 20 mg/100 g | study was interrupted |
| D | 12 | 1 | 57 mg/100 g | 2 metered doses/breast/day |
| E | 12 | 2 | 57 mg/100 g | 4 metered doses/breast/day |

At the end of a menstrual cycle, each patient received a single dose, after which serial blood samples were collected at 0, 0.5, 1, 1.5, 2, 3, 4, 6, 12, 18, 24, 36, 48, and 72 hours.

On the first day of the following menstruation, treatment, which consisted of daily application of the gel over two menstrual cycles, began. Blood samples were collected 24 hours following the morning application of gel on days 7, 20 and 25 of the first and second cycles. On the last day of administration, day 25 of the second menstrual cycle, serial blood samples were collected prior to application and at 0.5, 1, 1.5, 2, 3, 4, 6, 12, 18, 24, 36, 48, and 72 hours after application of the gel. The samples were analyzed for 4-hydroxy tamoxifen, estradiol, progesterone, FSH and LH.

Plasma concentrations of 4-hydroxy tamoxifen remained detectable 72 hours after the last gel application. Therefore, to ensure that data points were obtained until 4-hydroxy tamoxifen became undetectable in the blood, additional blood samples were collected from some participants at intervals up to 92 days following the last application of gel.

Table 6 displays the mean±standard deviation (SD) plasma concentrations of 4-hydroxy tamoxifen, with ranges in parentheses. A single 0.5 mg dose did not produce detectable plasma concentrations of 4-hydroxy tamoxifen, but 6 of 12 patients had detectable plasma concentrations (>5 pg/mL) after a single dose of 1 mg.

TABLE 6

Mean ± SD Plasma Concentrations of 4-hydroxy tamoxifen in Healthy Women Following Daily Cutaneous Administration for Two Menstrual Cycles

| Cycle | Day | Time after Application (hr) | 0.5 mg/day (n = 12)[1] | 1 mg/day (n = 8)[1] | 1 mg/day (n = 12)[2] | 2 mg/day (n = 12)[2] |
|---|---|---|---|---|---|---|
| | | | Mean ± SD (Range is indicated in parenthesis) in pg/mL | | | |
| First | 1 | 0 | (0-17.2) | (0-13.9) | (0-9.5) | (0-0) |
| | 7 | 24 | 6.4 ± 5.6 (<LOQ-16.8) | 15.2 ± 9.7 (<LOQ-26.8) | 14.4 ± 13.1 (<LOQ-37.9) | 26.9 ± 18.2 (8.9-71.3) |
| | 20 | 24 | 13.6 ± 7.9 (<LOQ-25.9) | 17.3 ± 9.5 (<LOQ-29.8) | 18.1 ± 15.8 (<LOQ-44.5) | 44.0 ± 29.2 (10.5-117.5) |
| | 25 | 24 | 23.9 ± 23.4 (<LOQ-73.1) | 15.5 ± 6.6 (6.4-25.0) | 19.8 ± 16.2 (6.2-57.0) | 45.4 ± 31.0 (17.9-120.1) |
| Second | 7 | 24 | 25.2 ± 16.1 (6.5-61.7) | 17.4 ± 11.2 (5.7-39.6) | 22.2 ± 16.4 (9.0-64.4) | 42.2 ± 24.8 (18.2-98.0) |
| | 20 | 24 | 15.7 ± 14.0 (<LOQ-52.3) | 14.8 ± 6.5 (5.4-24.8) | 24.4 ± 20.1 (<LOQ-65.4) | 38.9 ± 27.1 (18.7-119.7) |
| | 25 | 0[3] | 10.8 ± 9.9 (<LOQ-36.4) | 15.7 ± 17.1 (<LOQ-56.4) | 27.2 ± 20.8 (8.0-72.1) | 43.2 ± 27.7 (16.9-120.3) |
| | | 0.5 | 10.9 ± 7.4 (<LOQ-26.0) | 13.5 ± 9.1 (<LOQ-27.7) | 25.9 ± 18.7 (8.7-69.2) | 44.5 ± 29.9 (13.6-124.5) |
| | | 1 | 10.4 ± 7.8 (<LOQ-26.7) | 10.8 ± 6.6 (<LOQ-23.8) | 28.7 ± 19.5 (8.8-69.2) | 40.5 ± 25.1 (14.2-106.7) |
| | | 1.5 | 9.0 ± 8.2 (<LOQ-25.1) | 11.8 ± 8.0 (<LOQ-23.6) | 25.6 ± 17.8 (7.5-67.0) | 36.8 ± 21.1 (15.9-90.0) |
| | | 2 | 11.8 ± 9.5 (<LOQ-26.9) | 10.7 ± 6.9 (<LOQ-24.7) | 25.1 ± 18.0 (6.9-67.3) | 36.8 ± 21.6 (13.0-83.7) |
| | | 3 | 10.0 ± 7.9 (<LOQ-23.1) | 11.4 ± 7.9 (<LOQ-28.1) | 24.8 ± 20.5 (9.0-69.9) | 36.1 ± 20.6 (11.9-89.4) |
| | | 4 | 9.2 ± 8.3 (<LOQ-25.3) | 11.2 ± 7.3 (<LOQ-25.7) | 26.8 ± 23.3 (6.4-78.1) | 38.1 ± 21.2 (16.5-92.0) |
| | | 6 | 11.4 ± 8.5 (<LOQ-26.6) | 10.7 ± 6.4 (<LOQ-22.8) | 25.0 ± 18.2 (9.0-65.3) | 41.0 ± 29.1 (14.0-123.8) |
| | | 12 | 11.0 ± 9.7 (<LOQ-29.1) | 11.8 ± 7.8 (<LOQ-28.1) | 28.3 ± 22.9 (6.4-74.6) | 45.1 ± 30.6 (18.7-126.8) |
| | | 18 | 9.7 ± 8.8 (<LOQ-24.9) | 12.2 ± 8.3 (<LOQ-29.6) | 23.4 ± 17.4 (8.1-57.9) | 39.8 ± 25.5 (16.0-107.3) |
| | 26 | 24 | 12.4 ± 9.4 (<LOQ-34.4) | 18.6 ± 14.2 (<LOQ-40.1) | 26.0 ± 19.6 (8.9-61.9) | 44.0 ± 33.0 (15.8-132.5) |
| | | 36 | 10.9 ± 6.9 (5.0-25.8) | 13.4 ± 7.5 (<LOQ-25.4) | 25.7 ± 18.4 (8.8-61.3) | 42.1 ± 31.5 (15.1-129.3) |
| | 27 | 48 | 12.1 ± 6.5 (4.8-26.6) | 12.5 ± 6.0 (<LOQ-19.6) | 22.0 ± 16.0 (5.6-50.2) | 38.1 ± 25.3 (17.5-110.0) |
| | 28 | 72 | 9.9 ± 7.1 (<LOQ-22.3) | 9.9 ± 5.8 (<LOQ-19.6) | 18.9 ± 12.4 (5.6-37.8) | 33.2 ± 22.2 (17.7-98.0) |
| | | +5 days | — | 5.8 ± 5.2 (<LOQ-12.4) | 11.4 ± 8.2 (<LOQ-25.8) | 20.4 ± 17.3 (9.1-71.6) |
| | | +8 days | <LOQ | (<LOQ-17.4) | (0-14.8) | 10.8 ± 13.4 (<LOQ-52.0) |
| | | +12 days | (maximum 9.09) | (<LOQ-7.0) | (0-<LOQ) | (0-30.4) |
| | | +20 days | 0 | <LOQ | (0-<LOQ) | (0-<LOQ) |

[1] Gel concentration was 20 mg of 4-hydroxy tamoxifen per 100 g of gel.
[2] Gel concentration was 57 mg of 4-hydroxy tamoxifen per 100 g of gel.
[3] Timepoint 0 is 24 hours after the application on Day 24 and prior to the final application on Day 25.
LOQ = limit of quantification (<5 pg/mL)

FIG. 2 shows a plasma concentration-time curve, following the last administration on day 25 of the second menstrual cycle. Table 7 shows mean pharmacokinetic parameters that relate to the last administration, on day 25 of the second menstrual cycle.

TABLE 7

Mean Pharmacokinetic Parameters of 4-hydroxy tamoxifen in Healthy Women Following the Last Administration

| Parameter | Mean ± SD (Range is indicated in parenthesis) | | | |
|---|---|---|---|---|
| | 0.5 mg/day (n = 12)[a] | 1 mg/day (n = 8)[a] | 1 mg/day (n = 12)[b] | 2 mg/day (n = 12)[b] |
| $C_{max}$ (pg/mL) | 17.0 ± 8.5 (7.6-34.4) | 21.0 ± 14.0 (<LOQ-40.1) | 35.1 ± 22.4 (9.9-78.1) | 51.6 ± 31.7 (22.1-132.5') |
| $t_{max}$ (hr) | 40 ± 81 (0.5-288) | 24 ± 18 (0.5-48) | 12.8 ± 14.9 (1-36) | 11.8 ± 12.3 (0.5-36) |
| $t_{1/2}$ (hr) | — | — | (58-118) | (49-101) |
| $AUC_{0-24}$ (pg · hr/mL) | 256.3 ± 205.3 (24.6-651.1) | 300.9 ± 190.8 (0-693.6) | 619 ± 466 (187-1522) | 998 ± 653 (424-2778) |
| $C_{av} = AUC_{0-24}/24$ (pg/mL) | 10.7 ± 8.5 (1.0-27.1) | 12.5 ± 7.9 (0-28.9) | 25.8 ± 19.4 (7.8-63.4) | 41.6 ± 27.2 (17.7-115.8) |
| T (1stC < LOQ) (hr) | — | 274 ± 141 (144-480) | 236 ± 72 (144-384) | 326 ± 97 (192-480) |

[a]Gel concentration was 20 mg of 4-hydroxy tamoxifen per 100 g of gel.
[b]Gel concentration was 57 mg of 4-hydroxy tamoxifen per 100 g of gel.
$AUC_{0-24}$ = area under the concentration-time curve for 0-24 hours;
$C_{av}$ = Calculation of area under the curve over 24 hours ($AUC_{0-24}$) divided by 24 hours;
$C_{max}$ = maximal concentration in plasma;
$t_{1/2}$ = half-life;
T (1stC < LOQ) = first timepoint at which the plasma concentration was below the limit of quantification;
$t_{max}$ = time of maximal concentration in plasma.

The data are consistent with a dose response across the three doses tested (0.5, 1, and 2 mg). The more concentrated gel was better absorbed, by approximately double, than the less concentrated gel, based on AUC and $C_{av}$.

Biological tolerance was excellent in all 36 patients. The treatment did not affect FSH, LH, estradiol, or progesterone hormone levels during the menstrual cycles. Moreover, echographic examination of the ovaries at the end of treatment was normal in all patients, showing normal sized developing follicles. One patient developed an allergic reaction to the gel, and 10 reported facial acne (5 of which had a past history of acne).

In summary, this study indicates that the exposure to 4-hydroxy tamoxifen after topical application increases with dose, that plasma concentrations of 4-hydroxy tamoxifen are lower than typical estradiol concentrations (80 pg/mL), and that there is no detectable laboratory or clinical evidence of systemic effects.

EXAMPLE 4

Demonstration that Percutaneously Administered 4-Hydroxy Tamoxifen Causes Dose-Related Reductions in Tumor Tissue Proliferation Indexes This study demonstrates that percutaneously administered 4-hydroxy tamoxifen causes dose-related reductions in breast tumor tissue proliferation indexes. It is the first direct comparison of 4-hydroxy tamoxifen gel with tamoxifen and untreated controls on biological end points of breast cancer in humans. The results show that percutaneous administration of 4-hydroxy tamoxifen gel for 2-3 weeks produces dose-dependent reductions in tumor tissue proliferation indexes (Ki-67 and PCNA) in postmenopausal women scheduled to undergo surgery for breast cancer, with approximate equivalence between the 2.0 mg/day 4-hydroxy tamoxifen dose and 20 mg/day oral tamoxifen. Estrogen and progesterone receptor levels did not show dose-related reductions with 4-hydroxy tamoxifen treatment. Plasma levels of 4-hydroxy tamoxifen were consistently higher in the oral tamoxifen group than in the 4-hydroxy tamoxifen gel groups, and tumor tissue concentrations of 4-hydroxy tamoxifen increased with increasing dose of 4-hydroxy tamoxifen gel.

The present study also provides information on the biologic processes underlying the effects of tamoxifen. The group receiving 2 mg percutaneous 4-hydroxy tamoxifen showed the same cytostatic effect on breast cancer cell proliferation as the oral tamoxifen group in spite of markedly lower plasma 4-hydroxy tamoxifen concentrations. This finding shows that a major effect of tamoxifen is locally mediated by estrogen receptors in tumor tissue.

Study Design

A randomized, open, parallel groups phase IIb study was designed to compare the effects of three dose levels of 4-hydroxy tamoxifen, oral tamoxifen and no treatment on markers of tumor proliferation (Ki-67 and PCNA). Ki-67 antigen was detected by MIB1 antibody and PCNA (Proliferative Cell Nuclear Antigen) was detected with PC-10 monoclonal antibody.

Patients

Participants in the study were postmenopausal women diagnosed with estrogen receptor positive invasive breast cancer, as determined by Trucut biopsy. Criteria for enrollment included age >50 years, histologically confirmed T1 or T2 estrogen receptor positive primary breast cancer, and fit for surgery within 1 month of the biopsy. Patients with inflammatory cancer, known metastasis or lymph node involvement were excluded as were patients with previous radiotherapy or chemotherapy and ongoing hormone replacement therapy (a minimum washout period of 8 days was observed before the Tru-cut biopsy). Other exclusion criteria were a history of thrombophlebitis requiring anticoagulant treatment, retinopathy, cutaneous allergy to alcohol or mammary dermatitis contraindicating the application of a gel.

Patients were randomized to one of five treatment groups: 0.5 mg/d 4-OHT (0.5 ml gel [0.25 mg 4-OHT] applied to each breast daily); 1.0 mg/d 4-OHT (1 ml gel [0.5 mg 4-OHT] applied to each breast daily); 2.0 mg/d 4-OHT (2 ml gel [1.0 mg 4-OHT] applied to each breast daily); oral tamoxifen (20 mg/d as a single dose) or no treatment (untreated control). Patients were scheduled for tumor resection surgery with curative intent between day 15 and day 22 after the start of treatment. On the day prior to surgery, a blood sample was also obtained for determination of 4-OHT concentrations. On the day of surgery, patients were reassessed for concomitant therapy, concomitant conditions, hematology, biochemistry, plasma 4-OHT, estrone (E1), and estradiol (E2) concentrations.

Tumor Sampling

A Tru-cut/core biopsy taken at the first clinic attendance for diagnostic purposes was used as the pre-randomization tumor sample. A post-treatment specimen was obtained at definitive surgical resection. All of the tissue samples were fixed in 3.7% formalin immediately after removal, then embedded in paraffin wax for sectioning and subsequent analysis of biological markers. Tumor extracts (before and after treatment) were also stored in liquid nitrogen for subsequent assay of estrogen and progesterone receptors, as well as levels of 4-OHT.

Analysis of Tumor Marker Expression

Proliferation-Associated Antigen Expression.

Ki67 and Proliferating Cell Nuclear Antigen (PCNA) labeling indices (LI) were assessed on paraffin embedded sections of the pre- and post-treatment tissue specimens. The Ki67 antigen was assessed using the monoclonal antibody MIB 1 (DAKO, Denmark) as used in routine conditions in pathology. Anti-PCNA (DAKO) completed the panel of antibodies used to analyze proliferation in fixed tissues. Detection was made without heat denaturation. Six serial sections were analyzed per case in order to standardize sampling. Analysis was performed with a computer assisted system. (Système microphotométrique à balayage automatique; Samba-Alcatel, Grenoble, France). For each preparation, optical density (OD) thresholds were determined using real microscopic images of the analyzed field as reference. Measurements of immunostaining were performed at ×25. Twenty fields were analyzed for each section. Stained nuclear surface was determined (segmentation and thresholding) and a LI scored (stained cells/counterstained elements). OD immunostaining was expressed in arbitrary units. Control of immunostaining quantitative analysis and reproducibility of the procedure were performed: —by comparison to iterative measurements done on the same preparations, —by comparison to measurements compiled on six sequential sections of the same specimen. Evaluation of tissue variations in immunostaining quantitative analysis was performed by comparing the OD immunostaining measurements of 20 fields taken from nonconsecutive sections from each specimen. The intensity of PCNA immunoreactivity displayed by actively proliferating cells in lymph nodes (centroblasts) served as a reference for thresholds positive staining in breast tissues. Results were expressed as LI.

Estrogen and Progesterone Receptor Expression.

Estrogen (ER) and progesterone (PgR) receptor concentrations were assayed in tumor tissue before and after treatment with either ligand binding assay (LBA) using the Dextran-Coated Charcoal method (Korenman, 1974) and/or by immunohistochemical (ICH) method on paraffin-embedded sections. The cut-off for ER positivity was more than 10 fmol/mg measured using radioimmunoassay or more than 10% of tumoral cells labeled by an immunoenzymatic assay (Bevitt, 1997).

4-OHT Assay.

Concentrations of 4-OHT in plasma, tumor tissue, and normal tissue were performed using Gas Chromatography (GC) combined with Mass Spectrometry (MS) used in the Negative Ion Chemical Ionization-mode (NICI) (Girault, 1993). The quantification limits of the method were 5 pg/ml for the plasma and 50 pg/g for tissue samples respectively. Tumor extracts and normal breast tissue obtained at the time of surgery (after treatment) were stored in liquid nitrogen until subsequent assay of 4-OHT.

Statistical Analysis

Based on the planned sample size of 14 patients in the control group and 42 patients (3 groups) assigned to 4-OHT gel, this study had good power (90%) to detect a hypothesized 50% greater relative decrease in Ki-67 labeling index in the 4-OHT group than in the no treatment group using a two-sided test with 5% type I error. The primary efficacy endpoint was change in tumor proliferation marker expression. Other study variables were considered secondary endpoints. This "per protocol" analysis included only those who received at least 13 days of treatment, completed the end of treatment assessment for the primary endpoint, and had no significant protocol deviations or violations.

Treatment group comparisons were made using analysis of variance (ANOVA). The Kruskal-Wallis test was used in cases where the distribution of the data was non-symmetric/non-normal. Categorical variables were analyzed using Fisher's exact test. Hypothesis testing was conducted at the $\alpha=0.05$ significance level adjusted for multiple comparisons. Inferences fell into the following categories for the variables measured: —testing for differences among the five treatment groups; —examining differences among the three dose levels of 4-OHT; —examining differences between each dose level of 4-OHT and oral tamoxifen.

Results

Patient Characteristics.

A total of 55 patients were enrolled in the trial. Six patients were excluded from the analysis: one (in the 4-OHT 1.0 mg/d group) withdrew her consent, one (0.5 mg/d) was lost to follow-up, one (2.0 mg/d) was estrogen receptor negative at the start of the study, one (0.5 mg/d) received hormone replacement therapy, and two (0.5 and 1.0 mg/d) discontinued their treatment after only 6 and 12 days. Therefore, a total of 49 patients were evaluable for efficacy. Groups were well balanced with respect to tumor size, duration of amenorrhea, and tumor grade at surgery. Patients in the untreated control group were older than those in the active treatment groups (Table 7).

TABLE 7

| | | | | | Median (min:max) | |
|---|---|---|---|---|---|---|
| variable | Control | Oral Tam (20 mg/d) | 4-OHT gel (0.5 mg/d) | 4-OHT gel (1 mg/d) | 4-OHT gel (2 mg/d) | Total | P |

Geographic parameters of the studied population

| variable | Control | Oral Tam (20 mg/d) | 4-OHT gel (0.5 mg/d) | 4-OHT gel (1 mg/d) | 4-OHT gel (2 mg/d) | Total | P |
|---|---|---|---|---|---|---|---|
| n (patients) | 11 | 11 | 8 | 9 | 10 | 49 | |
| Age (years) | 72 | 62 | 65 | 64 | 61.5 | 65 | 0.07 |
| | 58:88 | 57:83 | 54:78 | 50:70 | 52:79 | 50:88 | |
| BMI (kg/m$^2$) | 24.6 | 25 | 24.7 | 25.9 | 23.6 | 24.7 | 0.88 |
| | 19.5:33.9 | 19.7:35.5 | 20.6:40.4 | 19.6:30.8 | 21.5:35.5 | 19.5:40.4 | |
| Tumor | | | | | | | |
| Left | 6 | 3 | 5 | 1 | 8 | 23 | 0.018 |
| Right | 5 | 8 | 3 | 8 | 2 | 26 | |
| Amenorrhea (years) | 21 | 10 | 14.7 | 9 | 12.5 | 13.3 | 0.40 |
| | 5:31.7 | 5:34 | 2:23.3 | 1:33 | 2:31.2 | 1:34 | |
| Tumor size (cm) | 1.5 | 1.5 | 2.0 | 2.0 | 1.75 | 2.0 | 0.90 |
| | 1.0:2.5 | 1.0:10.0 | 1.0:2.5 | 1.0:3.0 | 1.0:4.0 | 1.0:10.0 | |
| Grading | | | | | | | |
| I | 4 | 3 | 1 | 3 | 4 | | |
| II | 4 | 7 | 6 | 4 | 5 | | |
| III | 3 | 1 | 1 | 2 | 0 | — | — |
| pN+ specimen | 5 (45%) | 4 (36%) | 3 (38%) | 3 (33%) | 5 (50%) | — | — |

Proliferation-Associated Antigen Expression.

After adjusting for baseline levels, tumor tissue Ki-67 LIs after treatment differed significantly among the five groups (Table 8). Treated patients (4-OHT [all doses] and oral tamoxifen) had significantly lower mean Ki-67 LI scores compared to the untreated group (P=0.0054). Mean Ki-67 LI score after treatment was dose-dependent for the 4-OHT treatment groups. Moreover, a dose response relationship with approximate equivalence between the 4-0 HT 2.0 mg/d group and the oral tamoxifen group is demonstrated in Table 9A which shows the percentage of patients who had decreases in Ki-67 LI of $\geq 1$, $\geq 2$, or $\geq 3$ arbitrary units (%). There were no significant differences in Ki-67 labeling between tamoxifen and any dose of 4-OH. The tumor tissue response to the various treatments measured by PCNA LI paralleled that that assessed by the Ki-67 LI (Table 8, 9B). After treatment, tumor tissue PCNA LI for the four treated groups differed significantly, from the untreated control (P=0.002). As was seen with Ki-67 LIs, the percentage of patients who had decreases in PCNA index of $\geq 1$, $\geq 2$, or $\geq 3$ units (%) demonstrated a strong treatment effect of 4-OHT especially for the 4-OHT 1 and 2 mg/d groups, relative to untreated controls and showed approximate equivalence with oral tamoxifen (Table 9B). There were no significant differences in PCNA labeling between tamoxifen and any dose of 4-OHT. Response defined as a tumor having a PCNA LI or Ki-67 LI decrease of 3 arbitrary units demonstrated a tendency to increase with 4-OHT dosage. However, sample size was not sufficient to demonstrate significance for the relationship.

TABLE 8

Proliferative markers evolution according to the treatment

| | Control | Oral Tam (20 mg/d) | 4-OHT gel (0.5 mg/d) | 4-OHT gel (1 mg/d) | 4-OHT gel (2 mg/d) | Median (min:max) P* | P** | P*** |
|---|---|---|---|---|---|---|---|---|
| KI 67 Tru-cut (t) | 5 (2.4:9.0) | 6.7 (2.5:11.6) | 4.1 (0.99:12.8) | 6.8 (3.2:11.3) | 6.7 (3.5:10.3) | 0.44 | 0.48 | 0.24 |
| KI 67 Tumor (T) | 5.8 (2.7:12.4) | 2.8 (1.2:3.7) | 3.3 (0.8:8.99) | 3.3 (0.9:6.7) | 3.2 (2.05:4.8) | 0.0054 | 0.42 | 0.98 |
| Δ (t-T) | 0.28 (−2.5:8.4) | −3.8 (−10.2:1.0) | −0.8 (−4.1:1.9) | −4.5 (−5.9:1.1) | −3.9 (−7:−0.6) | — | — | — |
| PCNA Tru-cut (t) | 11.4 (3.3:14.7) | 7.8 (1.8:15.1) | 7.2 (4.6:9.6) | 11 (5.2:16.2) | 6.9 (5.9:11.4) | 0.12 | 0.11 | 0.04 |
| PCNA Tumor (T) | 11.9 (3.6:15.2) | 3.0 (1.4:7.6) | 4.6 (2.3:5.3) | 6.3 (4.0:8.2) | 4.5 (0.7:9.1) | 0.002 | 0.19 | 0.19 |
| Δ (t-T) | 0.54 (−0.81:2.9) | −2.9 (−9.4:0.12) | −2.2 (−7.3:0.61) | −4.4 (−11:2.9) | −4.2 (−7.4:2.2) | — | — | — |

P*: Kruskal-Wallis test between the 5 groups
P**: Kruskal-Wallis test between the 4 groups with oral Tam
P***: Kruskal-Wallis test between the 3 groups with 4 OHT gel

TABLE 9

Percentage of Patients Exhibiting a Decrease in Ki67/MIB1 Index (A) or in PCNA index (B) according to the treatment

|  | Control N = 11 | Oral Tam (20 mg/d) N = 11 | 4-OHT gel (0.5 mg/d) N = 8 | 4-OHT gel (1 mg/d) N = 9 | 4-OHT gel (2 mg/d) N = 10 |
|---|---|---|---|---|---|
| A | | | | | |
| ≧1.0 Unit Decrease | 40% | 90% | 50% | 89% | 87% |
| ≧2.0 Unit Decrease | 20% | 70% | 25% | 78% | 62% |
| ≧3.0 Unit Decrease | 0% | 60% | 25% | 56% | 62% |
| B | | | | | |
|  | Control N = 11 | Oral Tam (20 mg/d) N = 11 | 4-OHT gel (0.5 mg/d) N = 8 | 4-OHT gel (1 mg/d) N = 8 | 4-OHT gel (2 mg/d) N = 10 |
| ≧1.0 Unit Decrease | 0% | 73% | 75% | 87% | 78% |

TABLE 9-continued

Percentage of Patients Exhibiting a Decrease in Ki67/MIB1 Index (A) or in PCNA index (B) according to the treatment

|  | Control N = 11 | Oral Tam (20 mg/d) N = 11 | 4-OHT gel (0.5 mg/d) N = 8 | 4-OHT gel (2 mg/d) N = 10 |
|---|---|---|---|---|
| ≧2.0 Unit Decrease | 0% | 73% | 50% | 87% | 78% |
| ≧3.0 Unit Decrease | 0% | 45% | 37% | 75% | 67% |

ER Expression.

Using RIA, pretreatment ER concentrations were statistically similar across the groups with the mean group values ranging from 5 to 56 fmol/mg. Individual values showed a wide range (9 up to 321 fmol/mg). Treatment of ER-positive tumors with tamoxifen or 4-OHT resulted in a significant decrease (P=0.012) in ER concentration relative to the untreated control group. Using ICH, ER concentration (% of labeled cells) demonstrated the same median value at baseline (70 to 85%) across groups and showed no statistically significant increasing trend after treatment in all groups.

PgR Expression.

RIA measurements of PgR were widespread at baseline and increased after treatment in all groups, with no statistical significance or dose related-pattern. PgR results with ICH measurements did not indicate any consistent effect of treatment or dose-related changes.

4-OHT Tissue and Plasma Concentrations (Table 10, FIG. 3).

4-OHT median concentration was roughly 2-fold higher in the oral tamoxifen group (4237 pg/g) compared to that in the 2.0 mg/d 4-OHT group (1698 pg/g). Despite an increase of median tissue 4-OHT concentrations (pg/g) according to the percutaneous dose delivered (687, 1377 and 1698 pg/g for 0.5, 1 and 2 mg/d respectively), the difference between the three groups was not statistically significant (P=0.13). Non tumoral tissue 4-OHT concentration was about half those in tumor tissue in all except the 0.5 mg/d group. For 4-OHT median plasma concentration, there was a significant difference between the 4 treatments groups (P=0.0015) with a higher level for the oral tamoxifen group versus the 4-OHT gel groups (1495 pg/ml versus 31, 35 and 164 pg/ml respectively). Furthermore, there is a significant (P=0.035) increase of plasma 4 OHT with ascending 4-OHT percutaneous dose.

TABLE 10

4 OHT concentration in tumor, normal breast tissue and plasma

| 4-OHT | Control n = 11 | Oral Tam (20 mg/d) n = 11 | OHT gel (0.5 mg/d) n = 8 | OHT gel (1.0 mg/d) n = 9 | OHT gel (2.0 mg/d) n = 10 | * | ** | *** |
|---|---|---|---|---|---|---|---|---|
| Tumor pg/g | : | 4237 2388:7386 | 687 83:1978 | 1377 556:2955 | 1698 327:5123 | — | 0.0003 | 0.13 |
| Breast pg/g | : | 2038 1058:4461 | 528 83:3126 | 278 73:777 | 762 141:2080 | — | 0.0024 | 0.36 |
| Plasma pg/ml | : | 1495 32:1995 | 31 18:144 | 35 20:84 | 164 31:306 | — | 0.0015 | 0.035 |
| Plasma E2 pg/ml | 9.7 | 8.28 | 11 | 9 | 20 | 0.55 | — | — | p*: Kruskal-Wallis test between the 5 groups
p**: Kruskal-Wallis test between the 4 groups with oral Tam
p***: Kruskal-Wallis test between the 3 groups with 4-OHT gel

CITED PUBLICATIONS

Each of the following cited references is incorporated herein in its entirety.

Barrat, J., B. de Lignillres, L. Marpeau, L. Larue, S. Fournier, K. Nahoul, G. Linares, H. Giorgi, and G. Contesso, Effet in vivo de l'administration locale de progestIIrone sur l'activitII mitotique des galactophores humains, J. Gynecol. Obstet. Biol. Reprod. 19:269-274 (1990) (French).

Bevitt D, Milton I D, Piggot N, Henry L, Carter M J, Toms G L, et al. New monoclonal antibodies to estrogen and progesterone receptors effective for paraffin section immunohistochemistry, J. Pathol., 183: 228-32 (1997).

Bronaugh and Maibach, Percutaneous Absorption: Drugs Cosmetics Mechanisms Methodology, Marcel Dekker 1999.

Carthew, P., P. N. Lee, R. E Edwards, R. T. Heydon, B. M. Nolan, E. A. Martin, Cumulative exposure to tamoxifen: DNA adducts and liver cancer in the rat, Arch. Toxicol., 75: 375-80 (2001).

Charlier, C., A. Chariot, N. Antoine, M. P. Merville, J. Gielen, V. Castronovo, Tamoxifen and its active metabolite inhibit growth of estrogen receptor-negative MDA-MB-435 cells, 49(3): 351-8 (1995).

Chemite, G., C. Varin, L. Delalonde, J. R. Pasqualini, Effect of promegestone, tamoxifen, 4-hydroxytamoxifen and ICT 164,384 on the oestrone sulphatase activity of human breast cancer cells, Anticancer Res., 13(4) 931-4 (July-August 1993).

Dietze, E. C., L. E. Caldwell, S. L. Grupin, M. Mancini, and V. L. Seewald, Tamoxifen, but not 4-hydroxytamoxifen initiates apoptosis in p53(−) normal human mammary epithelial cells by inducing mitochondrial depolarization, J. Biol. Chem., 276(7): 5384-94 (Feb. 16, 2001).

Fentiman, I. S., Tamoxifen and mastalgia. An emerging indication, Drugs 32: 477-80 (1986).

Fentiman, I. S., M. Caleffi, H. Hamed, and M. A. Chaudary, Dosage and duration of tamoxifen treatment for mastalgia: a controlled trial, British Journal of Surgery 75: 845-46 (1988).

Fentiman, I. S., M. Caleffi, H. Hamed, and M. A. Chaudary, Studies of tamoxifen in women with mastalgia, British Journal of Clinical Practice, Supplement 68, 43(11): 34-36 (1989)).

Fischer, W., K. Klokkers, A. Sendl-Lang, Transdermal system in the form of a patch comprising a tamoxifen derivative, U.S. Pat. No. 5,904,930.

Gerdes, J., H. Lenke, Baisch, H. H. Wacker, U. Schwab, H. Stein, Cell cycle analysis of a cell proliferation-associated human nuclear antigen defined by the monoclonal antibody Ki-67, J. Immunology, 133: 1710-15 (1984).

Giambiagi, N. and J. R. Pasqualini, Immunological differences between the estradiol-, tamoxifen and 4-hydroxytamoxifen estrogen receptor complexes detected by two monoclonal antibodies, J. Steroid Biochem., 30(1-6): 213-7 (1988).

Girault J, Istin B, Fourtillan J. B. Quantitative measurement of 4-Hydroxy Tamoxifen in human plasma and mammary tumours by combined Gas Chromatography/Negative Chemical Ionization Mass Spectrometry, Biol. Mass. Spectrom., 22:395-402 (1993).

Gura, T, Systems for identifying new drugs are often faulty, Science, 278: 1041-42 (1997).

IBIS Investigators, First results from the International Breast Cancer Intervention Study (IBIS-I): a randomised prevention trial, Lancet, 360(9336): 817-24 (2002).

Jordan, V. C., Metabolites of tamoxifen in animals and man: identification, pharmacology, and significance, Breast Cancer Res. Treat., 2(2) 123-38 (1982).

Korenman S G, Stevens R H, Carpenter L A, Robb M, Niswender G D, Sherman B M. Estradiol radioimmunoassay without chromatography: procedure, validation and normal values, J. Clin. Endocrinol Metab., 38:718-20 (1974).

Kuiper, G. G. J. M., B. Carlsson, K. Grandien, E. Enmark, J. Heggblad, S, Nilsson, J. Gustafsson, Comparison of the ligand binding specificity and transcript tissue distribution of estrogen receptors α and β, Endocrinology, 138:863-870 (1997).

Kuttenn, F. and P. Mauvais-Jarvis, Intratumoral levels and metabolism of 4-hydroxytamoxifen after percutaneous administration at the breast level, C.R. Acad. Sci. III. 300: 457-462 (1985) (French).

Malet C., A. Gompel, P. Spritzer, N Bricourt, N H Yaneva, I. Mowszowicz, F. Kutten and P Mauvais Jarvis, Tarnoxifen and hydroxytamoxifen isomers versus estradiol effects on normal human breast cells in culture, Cancer Research, 48: 7193-7199 (1988).

Malet, C., P. Spritzer, C. Cumins, D. Guillaumin, P. Mauvais-Jarvis, F. Kuttenn, Effect of 4-hydroxytamoxifen isomers on growth and ultrastructural aspects of normal human breast epithelial (HBE) cells in culture, J. Steroid Biochem. & Mol. Bio., 82: 289-96 (2002).

Mauvais-Jarvis, P., N. Baudot, D. Castaigne, P. Banzet, and F. Kuttenn, Trans-4-hydroxytamoxifen concentration and metabolism after local percutaneous administration to human breast, Cancer Research, 46:1521-1525 (1986).

Murphy, C. S., S. M. Langan-Fahey, R. McCague, and V. C. Jordan, Structure-function relationships of hydroxylated metabolites of tamoxifen that control the proliferation of estrogen-responsive T47D breast cancer cells in vitro, Mol. Pharmac. 38:737-743 (1990).

Nemani M, Linares-Cruz G, Bruzzoni-Giovanelli H, Roperch J P, Tuynder M, Bougueleret L, et al. Activation of the human homologue of the Drosophila sina gene in apoptosis and tumor suppression, Proc. Natl. Acad. Sci., 93: 9039-42 (1996).

Nomura, Y., H. Tashiro, F. Takaeko, Effects of antiestrogens and medroxyprogesterone acetate on the clonogenic growth of tamoxifen-sensitive and resistant human breast cancer cells, Jpn. J. Cancer Chemotherapy, 12(4): 844-50 (1985).

Pujol, H., J. Girault, P. Rouanet, S. Fournier, J. Grenier, J. Simony, J. B. Fourtillan, and J. L. Pujol, Phase 1 study of percutaneous 4-hydroxy-tamoxifen with analyses of 4-hydroxy-tamoxifen concentrations in breast cancer and normal breast tissue, Cancer Chemother. Pharmacol., 36:493-498 (1995).

Remington: The Science and Practice of Pharmacy, Alfonso R. Gennaro, Lippincott Williams & Wilkins, 2000, pp. 836-858.

Robertson and Katzenellenbogen, J. Org. Chem., 47: 2387 (1982).

Robertson, D. W., J. A. Katzenellenbogen, D. J. Long, E. A. Rorke and B. S. Katzenellenbogen, Tamoxifen antiestrogens. A comparison of the activity, pharmacokinetics, and metabolic activation of the cis and trans isomers of tamoxifen, J. Steroid Biochemistry, 16(1): 1-13 (1982).

Sauvez, F., D. Salin-Drouin, M. Attia, H. Bertheux, and R. Forster, Cutaneously applied 4-hydroxytamoxien is not carcinogenic in female rats. Carcinogenesis, 20: 843-50 (1999).

Schluter, C., M. Duchrow, C. Wohlensberg, M H G Becker, G. Key, H. D. Flag, The cell proliferation-associated antigen of antibody Ki-67: a very large, ubiquitous nuclear protein with numerous repeated elements representing a new kind of cell maintaining proteins, Cell Biology, 123: 513-22 (1993).

Waseem, N. H., D. P. Lane, Monoclonal antibody analysis of the proliferating cell nuclear antigen (PCNA): Structural conservation and the detection of the nucleolar form, J. Cell. Sci., 96: 121-9 (1990).

Wijayaratne, A. L., S. C. Nagel, L. A. Paige, D. J. Christensen, J. D. Norris, D. M. Fowlkes, and D. P. McDonnell, Comparative Analyses of Mechanistic Difference among Antiestrogens, Endocrinology, 140(12): 5828-5840 (1999).

What is claimed is:

1. A method of treating breast cancer, comprising percutaneously administering 4-hydroxy tamoxifen to a patient having breast cancer, wherein said 4-hydroxy tamoxifen is administered in a vehicle containing isopropyl myristate as a penetration enhancer, wherein the isopropyl myristate constitutes from about 0.5% to about 2.0% by weight of the composition, at a dose of 4-hydroxy tamoxifen of at least 0.5 mg/breast per day.

2. The method according to claim 1, comprising administering about 0.5 to 1.0 mg/breast of said 4-hydroxy tamoxifen to said patient per day.

3. The method according to claim 1, comprising administering about 0.5 mg/breast of said 4-hydroxy tamoxifen to said patient per day.

4. The method according to claim 1, comprising administering about 0.75 mg/breast of said 4-hydroxy tamoxifen to said patient per day.

5. The method according to claim 1, comprising administering about 1.0 mg/breast of said 4-hydroxy tamoxifen to said patient per day.

6. The method according to claim 1, wherein said 4-hydroxy tamoxifen is formulated in a pharmaceutical composition selected from the group consisting of a hydroalcoholic gel, a hydroalcoholic solution, a patch, an ointment, a cream, an emulsion (lotion), a powder and an oil.

7. The method according to claim 1, wherein said 4-hydroxy tamoxifen is formulated in a hydroalcoholic gel composition.

8. The method according to claim 7, wherein said hydroalcoholic gel composition comprises, in addition to said isopropyl myristate, an aqueous vehicle, an alcoholic vehicle and a gelling agent.

9. The method according to claim 8, wherein said composition further comprises a neutralizing agent.

10. The method according to claim 8, wherein the alcoholic vehicle comprises an alcohol selected from ethanol or isopropanol, and constitutes about 65% to 75% by weight of the composition.

11. The method according to claim 8, wherein the aqueous vehicle is a phosphate buffered solution, and constitutes about 25% to 35% by weight of the composition.

12. The method according to claim 9, wherein the gelling agent is selected from the group consisting of polyacrylic acid and hydroxypropylcellulose, and constitutes about 1.0% to 5% by weight of the composition.

13. The method according to claim 9, wherein the neutralizing agent is selected from the group consisting of sodium hydroxide, ammonium hydroxide, potassium hydroxide, arginine, aminomethylpropanol and tromethamine, and constitutes about 0.1% to 5% by weight of the composition.

14. The method according to claim 8, wherein said hydroalcoholic gel comprises ethyl alcohol, isopropyl myristate, and hydroxypropylcellulose.

15. The method according to claim 1, wherein said 4-hydroxy tamoxifen is formulated in an alcoholic solution.

16. The method according to claim 1, wherein the 4-hydroxy tamoxifen constitutes from about 0.01% to about 0.10% by weight of the composition.

17. The method according to claim 1, wherein said breast cancer is estrogen receptor-positive.

18. The method according to claim 1, wherein the isopropyl myristate constitutes an amount by weight of the composition selected from the group consisting of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9% or 2.0%.

19. The method according to claim 1, comprising administering about 1.0 to 2.0 mg/breast of said 4-hydroxy tamoxifen to said patient per day.

20. The method according to claim 1, comprising administering about 2.0 mg/breast of said 4-hydroxy tamoxifen to said patient per day.

* * * * *